United States Patent
Meguro

(10) Patent No.: US 12,274,416 B2
(45) Date of Patent: Apr. 15, 2025

(54) MEDICAL IMAGE PROCESSING APPARATUS, ENDOSCOPE SYSTEM, MEDICAL IMAGE PROCESSING METHOD, AND PROGRAM

(71) Applicant: FUJIFILM Corporation, Tokyo (JP)

(72) Inventor: Misaki Meguro, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 518 days.

(21) Appl. No.: 17/591,976

(22) Filed: Feb. 3, 2022

(65) Prior Publication Data

US 2022/0151467 A1   May 19, 2022

Related U.S. Application Data

(63) Continuation of application No. PCT/JP2020/032049, filed on Aug. 25, 2020.

(30) Foreign Application Priority Data

Sep. 3, 2019   (JP) .................... 2019-160463

(51) Int. Cl.
*A61B 1/00* (2006.01)
*G06T 7/00* (2017.01)
(Continued)

(52) U.S. Cl.
CPC .... *A61B 1/000096* (2022.02); *A61B 1/00045* (2013.01); *A61B 1/00055* (2013.01);
(Continued)

(58) Field of Classification Search
CPC .......... A61B 1/000096; A61B 1/00045; A61B 1/00055; G06V 10/25; G06V 10/82;
(Continued)

(56) References Cited

U.S. PATENT DOCUMENTS 5,740,801 A * 4/1998 Branson .................... G06T 7/20
                                                      600/407
2006/0074275 A1   4/2006 Davidson et al.
(Continued)

FOREIGN PATENT DOCUMENTS

CN    107788998 A    3/2018
CN    108135457 A    6/2018
(Continued)

OTHER PUBLICATIONS

International Search Report issued in PCT/JP2020/032049; mailed Oct. 6, 2020.
(Continued)

*Primary Examiner* — Timothy J Neal
*Assistant Examiner* — James Edward Boice
(74) *Attorney, Agent, or Firm* — Studebaker Brackett PLLC

(57) ABSTRACT

Provided are a medical image processing apparatus, an endoscope system, a medical image processing method, and a program that may support search using information on an unobserved region of interest. The medical image processing apparatus includes an image acquisition unit (40) that acquires an observation image (38); a display signal transmission unit (44) that transmits, to a display apparatus (400), a first display signal indicating the observation image; a region-of-interest detection unit (50) that detects a region of interest from the observation image; and an unobserved image storage unit (71) that stores an unobserved image satisfying an unobserved condition indicating that the region of interest is yet to be observed from the observation image in which the region of interest is detected.

25 Claims, 13 Drawing Sheets

(51) Int. Cl.
*G06V 10/25* (2022.01)
*G06V 10/82* (2022.01)
*G10L 15/22* (2006.01)

(52) U.S. Cl.
CPC ............ *G06T 7/0012* (2013.01); *G06V 10/25* (2022.01); *G06V 10/82* (2022.01); *G10L 15/22* (2013.01); *G06T 2207/10068* (2013.01); *G06T 2207/20081* (2013.01); *G06T 2207/20084* (2013.01); *G10L 2015/223* (2013.01)

(58) Field of Classification Search
CPC ......... G06T 7/0012; G06T 2207/10068; G06T 2207/20081; G06T 2207/20084; G10L 15/22; G10L 2015/223
USPC ........................................................ 600/103
See application file for complete search history.

(56) References Cited

U.S. PATENT DOCUMENTS

| | | | |
|---|---|---|---|
| 2008/0009669 A1 | 1/2008 | Ozawa et al. | |
| 2008/0103382 A1 | 5/2008 | Kimoto | |
| 2009/0022400 A1 | 1/2009 | Matsuzaki | |
| 2011/0243523 A1* | 10/2011 | Davidson | A61B 1/04 386/224 |
| 2012/0078045 A1 | 3/2012 | Sasaki et al. | |
| 2012/0123205 A1* | 5/2012 | Nie | A61B 5/0084 600/109 |
| 2012/0289777 A1* | 11/2012 | Chopra | A61B 5/6852 382/128 |
| 2015/0009311 A1 | 1/2015 | Sasaki et al. | |
| 2015/0045614 A1* | 2/2015 | Krivopisk | A61B 1/00055 600/103 |
| 2016/0048637 A1* | 2/2016 | Nishiyama | A61B 1/041 382/305 |
| 2016/0202895 A1* | 7/2016 | Okumura | G06F 3/04855 345/156 |
| 2016/0292498 A1* | 10/2016 | Miura | A61B 1/01 |
| 2018/0242817 A1 | 8/2018 | Imaizumi et al. | |
| 2018/0325356 A1 | 11/2018 | Tateshita et al. | |
| 2019/0114738 A1 | 4/2019 | Sonoda | |
| 2020/0058124 A1 | 2/2020 | Iwaki | |
| 2020/0129042 A1 | 4/2020 | Takahashi et al. | |
| 2020/0237184 A1 | 7/2020 | Shigeta | |
| 2021/0022586 A1* | 1/2021 | Mori | A61B 1/045 |

FOREIGN PATENT DOCUMENTS

| | | |
|---|---|---|
| JP | 2006-198106 A | 8/2006 |
| JP | 2006-293237 A | 10/2006 |
| JP | 2007-318431 A | 12/2007 |
| JP | 2009-027558 A | 2/2009 |
| JP | 2012-070938 A | 4/2012 |
| WO | 2017/073337 A1 | 5/2017 |
| WO | 2017/216922 A1 | 12/2017 |
| WO | 2018/198161 A1 | 11/2018 |
| WO | 2018/216617 A1 | 11/2018 |
| WO | 2019/078237 A1 | 4/2019 |

OTHER PUBLICATIONS

International Preliminary Report on Patentability and Written Opinion issued in PCT/JP2020/032049; issued Mar. 8, 2022.
An Office Action; "Notice of Reasons for Refusal," mailed by the Japanese Patent Office on Sep. 1, 2022, which corresponds to Japanese Patent Application No. 2021-543711 and is related to U.S. Appl. No. 17/591,976; with English language translation.
The extended European search report issued by the European Patent Office on Sep. 29, 2022, which corresponds to European Patent Application No. 208600221.1-1126 and is related to U.S. Appl. No. 17/591,976.
An Office Action mailed by China National Intellectual Property Administration on Jan. 27, 2025, which corresponds to Chinese Patent Application No. 202080058661.3 and is related to U.S. Appl. No. 17/591,976; with English language translation.

* cited by examiner

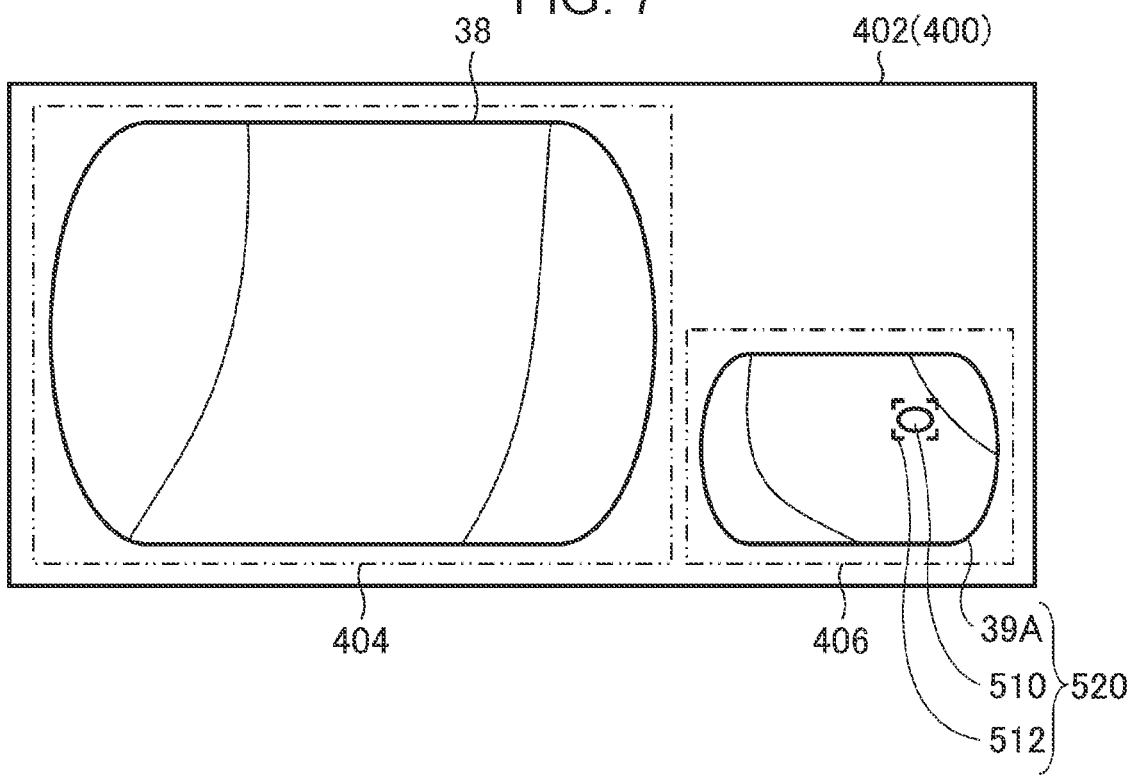
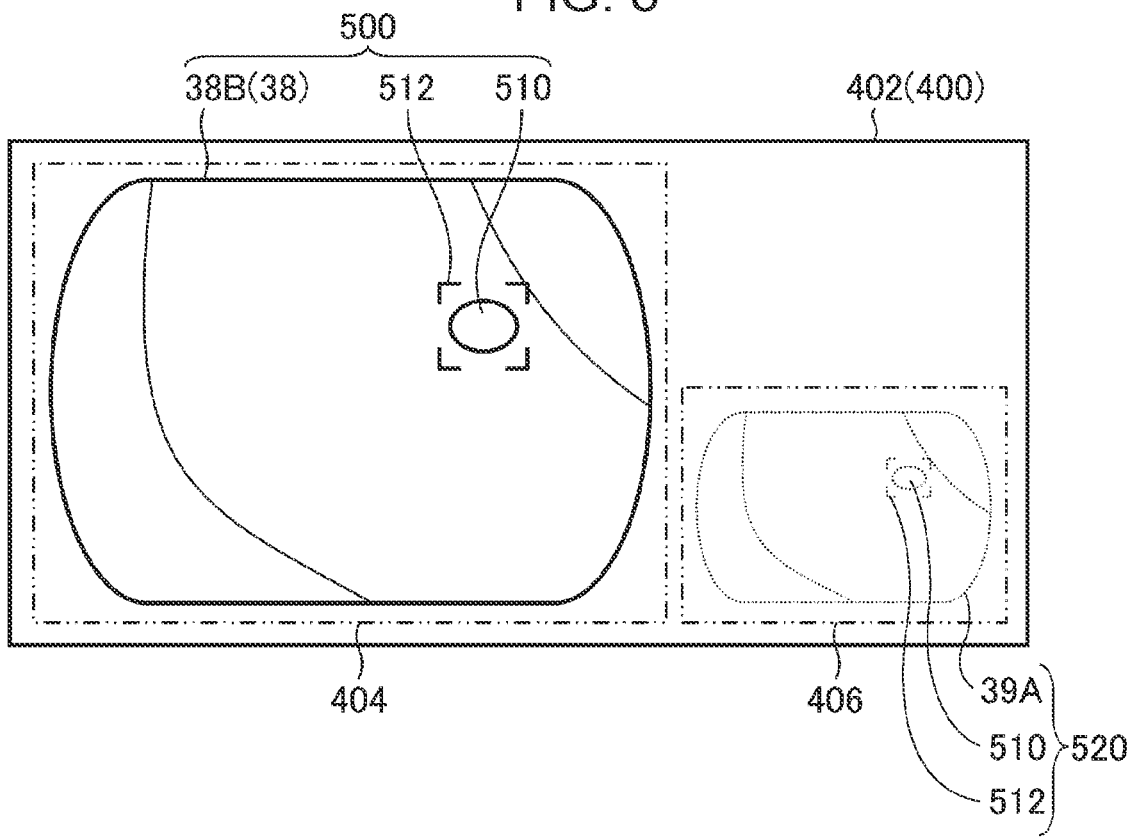

MEDICAL IMAGE PROCESSING APPARATUS, ENDOSCOPE SYSTEM, MEDICAL IMAGE PROCESSING METHOD, AND PROGRAM

CROSS-REFERENCE TO RELATED APPLICATIONS

The present application is a Continuation of PCT International Application No. PCT/JP2020/032049 filed on Aug. 25, 2020 claiming priority under 35 U.S.C § 119(a) to Japanese Patent Application No. 2019-160463 filed on Sep. 3, 2019. Each of the above applications is hereby expressly incorporated by reference, in its entirety, into the present application.

BACKGROUND OF THE INVENTION

1. Field of the Invention

The present invention relates to a medical image processing apparatus, an endoscope system, a medical image processing method, and a program.

2. Description of the Related Art

Systems that detect a lesion and that support diagnosis by introducing AI technology or the like to an endoscopic image or the like have been attracting attention for reducing the rate of overlooking a lesion and for leading to reduction of unnecessary bioscopy. Such a system notifies a physician by, for example, working in real time during execution of an endoscopic examination and displaying a screen of recognition results and the like. Note that AI is an abbreviation for Artificial Intelligence.

WO2018/198161A, WO2017/216922A, and WO2017/073337A describe endoscope systems that detect a candidate lesion region in an observation image on the basis of a feature quantity calculated from the observation image and that cause a display apparatus to display the detected candidate lesion region.

In the endoscope system described in WO2018/198161A, a marker image that emphasizes the position of the candidate lesion region is added to the observation image. The system changes a display manner of the marker image depending on the length of a period in which the candidate lesion region is continuously detected. Specifically, when the period in which the candidate lesion region is continuously detected reaches a predetermined period, emphasis processing is started.

The endoscope system described in WO2017/216922A stores observation images that are sequentially output from a video processor during the continuous detection period. When the continuous detection period is less than a predetermined period, after an elapse of the predetermined period, the system causes the stored observation images to be displayed in the reverse order of the order for storage, in a display region that is different from a display region for displaying an observation image.

The endoscope system described in WO2017/073337A temporarily stores a still image in a memory when the candidate lesion region is detected and notification processing is started. In response to turning on of an operation switch, the system adds a marker image to the still image that is temporarily stored in the memory and causes a display unit to display the still image.

JP2006-198106A describes an electronic endoscope apparatus that is to be inserted into a subject and to observe the interior of the subject. In the apparatus described in JP2006-198106A, automatically, a still image is temporarily stored in a memory in response to detection of an abnormal pixel. In addition, the apparatus displays, in a thumbnail display area, a thumbnail image of the still image that is temporarily stored in the memory.

SUMMARY OF THE INVENTION

A physician who has overlooked detection of a region of interest may notice that the region of interest has been overlooked by being notified that the region of interest is detected. The physician needs support using information on the overlooked region of interest when searching for the overlooked region of interest or the like. However, WO2018/198161A, WO2017/216922A, WO2017/073337A, and JP2006-198106A do not describe or suggest the information related to the overlooked region of interest.

The system described in WO2018/198161A performs emphasis processing on the lesion region or the like when the period in which the lesion region or the like is detected reaches the predetermined period to reduce the load on the physician who visually observes the candidate lesion region. On the other hand, the system described in WO2018/198161A does not include a constituent element that stores information on a candidate lesion region that has been overlooked.

The system described in WO2017/216922A stores one or more observation images during a period from start until interruption of detection of a region of interest and automatically displays the stored observation images after interruption of detection of the region of interest so as to reduce overlooking of a lesion part. On the other hand, sequentially and automatically re-displaying the observation images may lead to reduction of the physician's concentration, which may possibly lead to overlooking of the region of interest. In addition, the system described in WO2017/216922A does not include a constituent element that stores information on a candidate lesion region that has been overlooked.

The system described in WO2017/073337A temporarily stores the still image including the candidate lesion region in response to detection of the candidate lesion region and displays the still image in response to turning on of the operation switch. WO2017/073337A does not describe that the still image in which the candidate lesion region is detected is selectively stored, and the system described in WO2017/073337A is considered to store all the still images including the candidate lesion region. In such a case, it is difficult to determine whether a physician has observed the still image that is temporarily stored.

JP2006-198106A does not describe that the still image is selectively and temporarily stored in response to detection of the abnormal pixel, and the apparatus described in JP2006-198106A is considered to temporarily store all the still images in response to detection of the abnormal pixel. In such a case, it is difficult to determine whether a physician has observed the still image that is temporarily stored.

That is, in each of the systems and the like described in WO2018/198161A, WO2017/216922A, WO2017/073337A, and JP2006-198106A, support is difficult when a physician searches for a region of interest that has been overlooked and is yet to be observed.

The present invention has been made in view of the above circumstances, and an object thereof is to provide a medical image processing apparatus, an endoscope system, a medical image processing method, and a program that may support a search using information on the unobserved region of interest.

To achieve the above object, the following aspects of the invention are provided.

A medical image processing apparatus according to a first aspect is a medical image processing apparatus including: an image acquisition unit that acquires an observation image of a subject; a display signal transmission unit that transmits, to a display apparatus, a first display signal indicating the observation image; a region-of-interest detection unit that detects a region of interest from a frame image constituting the observation image; and an unobserved image storage unit that stores an unobserved image satisfying an unobserved condition indicating that the region of interest is yet to be observed from the frame image in which the region of interest is detected.

According to the first aspect, the frame image including the unobserved region of interest satisfying the unobserved condition from the observation image in which the region of interest is detected is stored. This may support a search for the unobserved region of interest using the unobserved image.

The observation image of the subject may be a moving image or a group of still images including a plurality of still images. Examples of the observation image include an endoscopic image captured by an endoscope.

The frame image is equivalent to a single still image included in the group of still images including the plurality of still images.

Examples of the unobserved region of interest include a region of interest on which a user has not performed an operation of an imaging apparatus, such as zooming.

According to a second aspect, the medical image processing apparatus according to the first aspect may include an unobserved condition determination unit that determines whether the frame image, in which the region of interest is detected by the region-of-interest detection unit, satisfies the unobserved condition.

According to the second aspect, the unobserved image may be determined from a plurality of frame images in which the region of interest is detected, on the basis of the unobserved condition.

In the second aspect, an unobserved condition setting unit that sets the unobserved condition is preferably included.

According to a third aspect, in the medical image processing apparatus according to the second aspect, in a case where a number of frame images including the same region of interest within a predetermined period is less than or equal to a predetermined number, the unobserved condition determination unit may determine that the unobserved condition is satisfied.

According to the third aspect, the number of frame images including the same region of interest may be used as the unobserved condition.

According to a fourth aspect, in the medical image processing apparatus according to the second or third aspect, in a case where a change amount between frame images is greater than or equal to a predetermined threshold value, the unobserved condition determination unit may determine that the unobserved condition is satisfied.

According to the fourth aspect, the change amount between frame images may be used as the unobserved condition.

According to a fifth aspect, in the medical image processing apparatus according to any one of the second to fourth aspects, in a case where the same region of interest remains in a given region on a screen within a predetermined period, the unobserved condition determination unit may determine that the unobserved condition is satisfied.

According to the fifth aspect, the position of the same region of interest on the screen may be used as the unobserved condition.

According to a sixth aspect, in the medical image processing apparatus according to any one of the second to fifth aspects, the display signal transmission unit may transmit, to the display apparatus, a second display signal indicating the unobserved image that is determined to satisfy the unobserved condition by the unobserved condition determination unit.

According to the sixth aspect, the unobserved image is displayed on the display apparatus. This may support a search for the unobserved region of interest using the unobserved image displayed on the display apparatus.

According to a seventh aspect, the medical image processing apparatus according to the sixth aspect may include a user input signal acquisition unit that acquires a user input signal transmitted in response to a user operation, in which, upon the user input signal acquisition unit acquiring a user input signal indicating displaying of an unobserved region of interest, the display signal transmission unit may transmit, to the display apparatus, the second display signal indicating the unobserved image.

According to the seventh aspect, upon acquisition of the user input signal, the display signal indicating the unobserved image is transmitted to the display apparatus. This may support a search for the unobserved region of interest using the unobserved image displayed on the display apparatus.

According to an eighth aspect, in the medical image processing apparatus according to the seventh aspect may include a first image processing unit that performs first image processing on the region of interest detected by the region-of-interest detection unit to generate a first image, in which the display signal transmission unit may transmit, to the display apparatus, a display signal indicating the first image as the first display signal.

According to the eighth aspect, the first image on which the first image processing is performed may be displayed on the display apparatus.

In the eighth aspect, a first image processing result storage unit that stores a result of the first image processing may be included.

The first image, or a combination of the observation image and information indicating the processing result of the first image processing associated with the observation image, may be used as the processing result of the first image processing.

According to a ninth aspect, the medical image processing apparatus according to the eighth aspect may include a second image processing unit that performs second image processing on the unobserved image to generate a second image, in which the display signal transmission unit may transmit, to the display apparatus, a display signal indicating the second image as the second display signal.

According to the ninth aspect, the second image obtained by performing the second image processing on the unobserved image may be displayed on the display apparatus.

According to a tenth aspect, in the medical image processing apparatus according to the ninth aspect, the first image processing unit may perform emphasis processing of the region of interest on the observation image, and the second image processing unit may perform emphasis processing on the unobserved image to increase an emphasis degree compared with an emphasis degree of the emphasis processing of the region of interest on the observation image.

According to the tenth aspect, the second image in which the emphasis degree is increased compared with the emphasis degree of the emphasis processing on the observation image may be displayed on the display apparatus. This makes it easier to view the region of interest in the second image.

According to an eleventh aspect, in the medical image processing apparatus according to the ninth or tenth aspect, the second image processing unit may perform the second image processing on each of a plurality of unobserved images, and the display signal transmission unit may transmit, to the display apparatus, a display signal corresponding to each of a plurality of second images as the second display signal.

According to the eleventh aspect, the plurality of unobserved images or the plurality of second images may be displayed on the display apparatus. This may enable a user to search for the region of interest in the observation image using the plurality of unobserved images or the plurality of second images.

According to a twelfth aspect, the medical image processing apparatus according to the eleventh aspect may include a selection unit that selects one or more unobserved images from among the plurality of unobserved images to be displayed on the display apparatus or selects one or more second images from among the plurality of second images to be displayed on the display apparatus.

According to the twelfth aspect, a user may set an unobserved image to be used for searching for the region of interest in the observation image from among the plurality of unobserved images or may set a second image to be used for searching for the region of interest in the observation image from among plurality of second images.

According to a thirteenth aspect, the medical image processing apparatus according to any one of the ninth to twelfth aspects may include a third image processing unit that performs third image processing on the unobserved image or a processing result of the second image processing to be displayed on the display apparatus.

According to the thirteenth aspect, the third image processing may be performed on the unobserved image or the second image.

According to a fourteenth aspect, the medical image processing apparatus according to the thirteenth aspect may include a third image processing result storage unit that stores a processing result of the third image processing.

According to the fourteenth aspect, the processing result of the third image processing may be stored.

The third image processing result storage unit may store a third image as the processing result of the third image processing. The third image processing result storage unit may store a combination a processing target image and information indicating the processing result of the third image processing associated with the processing target image as the processing result of the third image processing.

According to a fifteenth aspect, in the medical image processing apparatus according to the thirteenth or fourteenth aspect, the third image processing unit may edit the unobserved image upon the user input signal acquisition unit acquiring a user input signal indicating editing of the unobserved image or may edit the second image upon the user input signal acquisition unit acquiring a user input signal indicating editing of the second image.

According to the fifteenth aspect, the unobserved image or the second image may be edited upon acquisition of the user input signal.

According to a sixteenth aspect, in the medical image processing apparatus according to any one of the thirteenth to fifteenth aspects, the third image processing unit may transmit the unobserved image to an external apparatus upon the user input signal acquisition unit acquiring a user input signal indicating transmission of the unobserved image to the external apparatus or may transmit the second image to an external apparatus upon the user input signal acquisition unit acquiring a user input signal indicating transmission of the second image to the external apparatus.

According to the sixteenth aspect, the unobserved image or the second image may be transmitted to the external apparatus.

According to a seventeenth aspect, in the medical image processing apparatus according to any one of the thirteenth to sixteenth aspects, the third image processing unit may rearrange a plurality of unobserved images upon the user input signal acquisition unit acquiring a user input signal indicating rearranging of the plurality of unobserved images or may rearrange a plurality of second images upon the user input signal acquisition unit acquiring a user input signal indicating rearranging of the plurality of second images.

According to the seventeenth aspect, in a configuration in which the plurality of unobserved images or the plurality of second images are to be displayed on the display apparatus, the plurality of unobserved images, the plurality of second images, or the like may be rearranged.

According to an eighteenth aspect, in the medical image processing apparatus according to any one of the thirteenth to seventeenth aspects, the third image processing unit may delete the unobserved image upon the user input signal acquisition unit acquiring a user input signal indicating deletion of the unobserved image or may delete the second image upon the user input signal acquisition unit acquiring a user input signal indicating deletion of the second image.

According to the eighteenth aspect, the unobserved image or the second image may be deleted upon acquisition of the user input signal.

According to a nineteenth aspect, in the medical image processing apparatus according to any one of the sixth to eighteenth aspects, the display signal transmission unit may stop transmitting the second display signal after an elapse of a predetermined period from a transmission timing of the second display signal.

According to the nineteenth aspect, the unobserved image or the second image may be automatically hidden.

According to a twentieth aspect, in the medical image processing apparatus according to any one of the sixth to eighteenth aspects, the display signal transmission unit may stop transmitting the second display signal when the unobserved region of interest is displayed on the display apparatus.

According to the twentieth aspect, the unobserved image or the second image may be hidden when a search target region of interest is found.

According to a twenty-first aspect, the medical image processing apparatus according to the first to twentieth aspects may include a user operation unit operated by a user, in which the user input signal acquisition unit may acquire a user input signal transmitted in response to an operation performed by the user on the user operation unit.

According to the twenty-first aspect, the user input signal may be transmitted in response to the operation performed by the user.

According to a twenty-second aspect, the medical image processing apparatus according to any one of the first to twenty-first aspects may include a voice acquisition unit that acquires a voice of a user, in which the user input signal acquisition unit may acquire a user input signal indicating the voice of the user acquired by the voice acquisition unit.

According to the twenty-second aspect, the user input signal may be transmitted in response to the voice of the user.

According to a twenty-third aspect, the medical image processing apparatus according to any one of the first to twenty-second aspects may include an observed image storage unit that stores an observed image indicating that the region of interest has been observed from the frame image in which the region of interest is detected by the region-of-interest detection unit.

According to the twenty-third aspect, the observed image is stored. This may support a search for the observed region of interest using the observed image.

According to a twenty-fourth aspect, the medical image processing apparatus according to any one of the first to twenty-third aspects may include a notification unit that notifies detection of the region of interest in the observation image.

According to twenty-fourth aspect, a user may notice the detection of the region of interest.

An endoscope system according to a twenty-fifth aspect is an endoscope system including: an endoscope; an endoscope control apparatus that controls the endoscope; and a medical image processing apparatus that performs processing on an endoscopic image acquired by the endoscope, in which the medical image processing apparatus includes: an image acquisition unit that acquires an observation image of a subject; a display signal transmission unit that transmits, to a display apparatus, a first display signal indicating the observation image; a region-of-interest detection unit that detects a region of interest from a frame image constituting the observation image; and an unobserved image storage unit that stores an unobserved image satisfying an unobserved condition indicating that the region of interest is yet to be observed from the frame image in which the region of interest is detected.

According to the twenty-fifth aspect, substantially the same effects as those of the first aspect can be obtained.

In the twenty-fifth aspect, an item that is substantially the same as an item specified in the second to twenty-fourth aspects may be combined as appropriate. In this case, a constituent element that performs or implements a process or a function specified in the medical image processing apparatus can be grasped as a constituent element of the endoscope system that performs or implements the process or function corresponding thereto.

A medical image processing method according to a twenty-sixth aspect is a medical image processing method including: an image acquisition step of acquiring an observation image of a subject; a display signal transmission step of transmitting, to a display apparatus, a first display signal indicating the observation image; a region-of-interest detection step of detecting a region of interest from a frame image constituting the observation image; and an unobserved image storage step of storing an unobserved image satisfying an unobserved condition indicating that the region of interest is yet to be observed from the frame image in which the region of interest is detected.

According to the twenty-sixth aspect, substantially the same effects as those of the first aspect can be obtained.

In the twenty-sixth aspect, an item that is substantially the same as an item specified in the second to twenty-fourth aspects may be combined as appropriate. In this case, a constituent element that performs or implements a process or a function specified in the medical image processing apparatus can be grasped as a constituent element of the medical image processing method that performs or implements the process or function corresponding thereto.

A program according to a twenty-seventh aspect is a program for causing a computer to implement: an image acquisition function of acquiring an observation image of a subject; a display signal transmission function of transmitting, to a display apparatus, a first display signal indicating the observation image; a region-of-interest detection function of detecting a region of interest from a frame image constituting the observation image; and an unobserved image storage function of storing an unobserved image satisfying an unobserved condition indicating that the region of interest is yet to be observed from the frame image in which the region of interest is detected.

According to the twenty-seventh aspect, substantially the same effects as those of the first aspect can be obtained.

In the twenty-seventh aspect, an item that is substantially the same as an item specified in the second to twenty-fourth aspects may be combined as appropriate. In this case, a constituent element that performs or implements a process or a function specified in the medical image processing apparatus can be grasped as a constituent element of the program that performs or implements the process or function corresponding thereto.

According to the present invention, the frame image including the unobserved region of interest satisfying the unobserved condition from the observation image in which the region of interest is detected is stored. This may support a search for the unobserved region of interest using the unobserved image.

BRIEF DESCRIPTION OF THE DRAWINGS

FIG. 7 schematically illustrates a screen in a case where a user input signal indicating displaying of an unobserved region of interest is acquired;

FIG. 8 schematically illustrates an unobserved image display region that is hidden;

DESCRIPTION OF THE PREFERRED EMBODIMENTS

Figure 1:
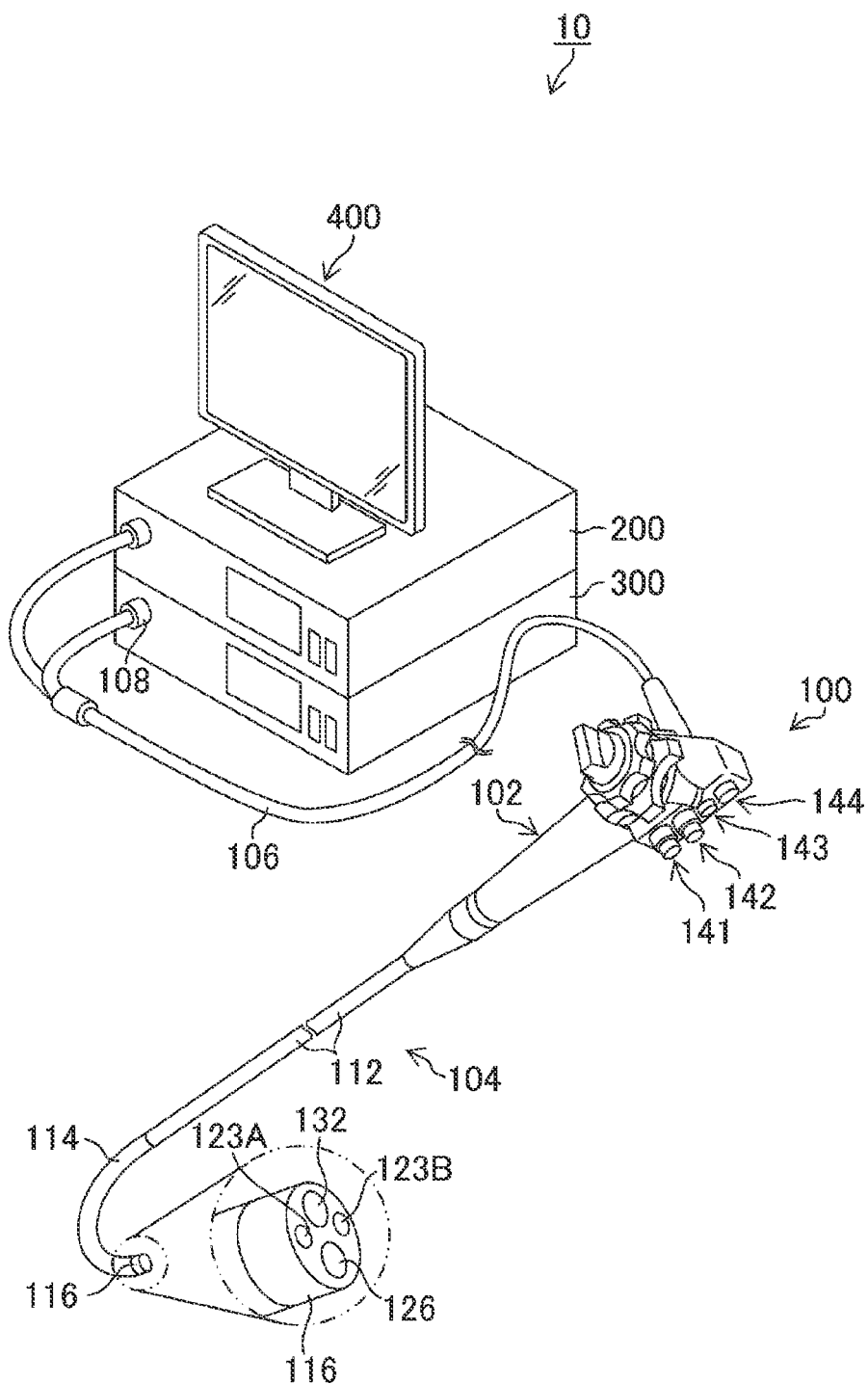
FIG. 1 illustrates an overall configuration of an endoscope system including an image processing apparatus according to embodiments.

Now, preferred embodiments of the present invention will be described below in detail with reference to the accompanying drawings. Identical constituent elements will be herein denoted by identical reference numerals, and redundant description will be omitted as appropriate.

Overall Configuration of Endoscope System

FIG. 1 illustrates an overall configuration of an endoscope system including an image processing apparatus according to the embodiments. An endoscope system 10 includes an endoscope main body 100, a processor apparatus 200, a light source apparatus 300, and a monitor 400. Note that FIG. 1 also illustrates an enlarged view of part of a tip rigid part 116 that is included in the endoscope main body 100.

Configuration Example of Endoscope Main Body

The endoscope main body 100 includes a handheld operation part 102 and an insertion part 104. A user holds the handheld operation part 102 for operation and inserts the insertion part 104 into a subject's body to observe the interior of the subject's body. Note that the user is equivalent to a physician, a surgeon, and the like. In addition, the subject herein is equivalent to a patient and an examinee.

The handheld operation part 102 includes an air/water supply button 141, a suction button 142, a function button 143, and an imaging button 144. The air/water supply button 141 receives operations for air supply instruction and water supply instruction.

The suction button 142 receives a suction instruction. Various functions are assigned to the function button 143. The function button 143 receives instructions of the various functions. The imaging button 144 receives an imaging instruction operation. Imaging includes capturing a moving image and capturing a still image.

The handheld operation part 102 functions as a user input unit. Although omitted from the illustration, a foot switch may be further included as the user input unit. The foot switch includes a pedal, a pedal instruction part, and a cable. The cable is connected to the processor apparatus 200.

The user may transmit a user input signal to the processor apparatus 200 by operating the foot switch. The processor apparatus 200 acquires the user input signal transmitted from the foot switch and performs processing corresponding to the user input signal.

The insertion part 104 includes a soft part 112, a bending part 114, and the tip rigid part 116. The soft part 112, the bending part 114, and the tip rigid part 116 are disposed in this order from the handheld operation part 102 side. That is, the bending part 114 is connected to a base end side of the tip rigid part 116, the soft part 112 is connected to a base end side of the bending part 114, and the handheld operation part 102 is connected to a base end side of the insertion part 104.

The user can operate the handheld operation part 102, bend the bending part 114, and change the direction of the tip rigid part 116 vertically and horizontally. The tip rigid part 116 includes an imaging part, an illumination part, and a forceps port 126.

FIG. 1 illustrates an imaging lens 132 that constitutes the imaging part. FIG. 1 further illustrates an illumination lens 123A and an illumination lens 123B that constitute the illumination part. Note that the imaging part is denoted by reference numeral 130 and illustrated in FIG. 2. In addition, the illumination part is denoted by reference numeral 123 and illustrated in FIG. 2.

Figure 2:
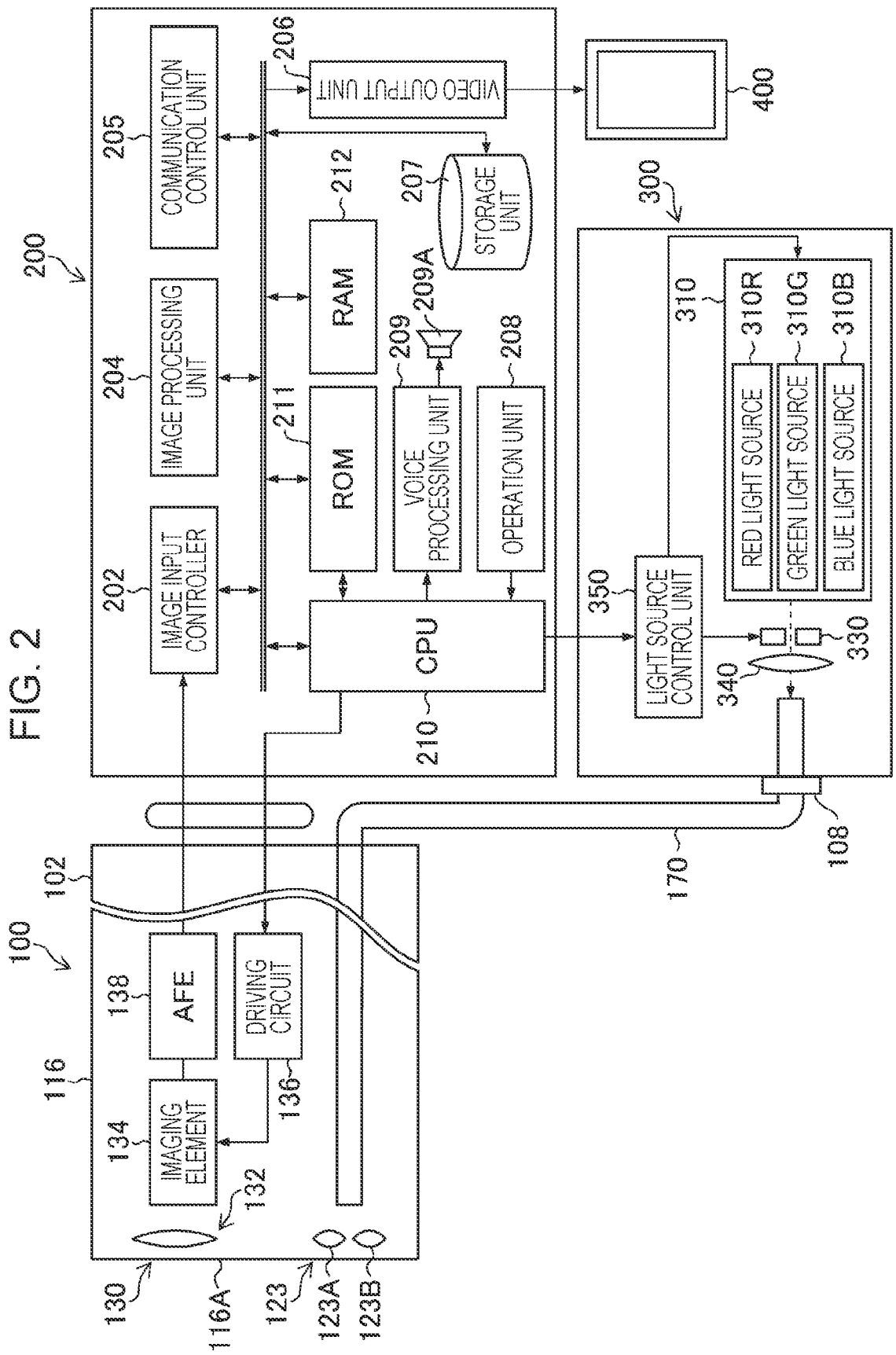
FIG. 2 is a functional block diagram of the endoscope system.

During observation and treatment, in accordance with an operation of an operation unit 208 illustrated in FIG. 2, at least any of white light or narrow-band light is output via the illumination lens 123A and the illumination lens 123B.

In response to an operation on the air/water supply button 141, wash water is emitted from a water supply nozzle, or a gas is emitted from an air supply nozzle. The wash water and gas are used for washing the illumination lens 123A and the like. Note that the water supply nozzle and the air supply nozzle are omitted from the illustration. The water supply nozzle and the air supply nozzle may be shared.

The forceps port 126 communicates with a pipe line. A treatment tool is to be inserted into the pipe line. The treatment tool is supported to be movable back and forth as appropriate. Necessary treatment is provided by using the treatment tool when extracting a tumor or the like, for example. Note that the pipe line that communicates with the forceps port 126 is omitted from the illustration.

FIG. 2 is a functional block diagram of the endoscope system. The endoscope main body 100 includes the imaging part 130. The imaging part 130 is disposed inside the tip rigid part 116. The imaging part 130 includes the imaging lens 132, an imaging element 134, a driving circuit 136, and an analog front end 138. Note that AFE in FIG. 2 is an abbreviation for Analog Front End.

The imaging lens 132 is disposed on a tip-side end surface 116A of the tip rigid part 116. The imaging element 134 is disposed at a position opposite to the tip-side end surface 116A of the imaging lens 132. A CMOS image sensor is used as the imaging element 134. A CCD image sensor may also be used as the imaging element 134. Note that CMOS is an abbreviation for Complementary Metal-Oxide Semiconductor, and CCD is an abbreviation for Charge Coupled Device.

A color imaging element is used as the imaging element 134. Examples of the color imaging element includes an imaging element including color filters corresponding to RGB. Note that R, G, and B are initials of Red, Green, and Blue.

A monochrome imaging element may also be used as the imaging element 134. When a monochrome imaging element is used as the imaging element 134, the imaging part 130 may perform frame sequential or color sequential imaging by switching a wavelength range of incident light of the imaging element 134.

On the basis of a control signal transmitted from the processor apparatus 200, the driving circuit 136 supplies, to the imaging element 134, various timing signals that are necessary for operation of the imaging element 134.

The analog front end 138 includes an amplifier, a filter, and an A/D converter. Note that A and D are initials of analog and digital. The analog front end 138 performs processing such as amplification, denoising, or analog/digital conversion on an output signal of the imaging element 134. An output signal of the analog front end 138 is transmitted to the processor apparatus 200.

An optical image of an observation target is formed on a light receiving plane of the imaging element 134 via the imaging lens 132. The imaging element 134 converts the optical image of the observation target into an electric signal. The electric signal output from the imaging element 134 is transmitted to the processor apparatus 200 via a signal line.

The illumination part 123 is disposed in the tip rigid part 116. The illumination part 123 includes the illumination lens 123A and the illumination lens 123B. The illumination lens 123A and the illumination lens 123B are disposed at positions adjacent to the imaging lens 132 on the tip-side end surface 116A.

The illumination part 123 includes a light guide 170. An emission end of the light guide 170 is disposed at a position opposite to the tip-side end surface 116A of the illumination lens 123A and the illumination lens 123B.

The light guide 170 is inserted into the insertion part 104, the handheld operation part 102, and a universal cable 106 illustrated in FIG. 1. An incident end of the light guide 170 is disposed inside a light guide connector 108. Note that the endoscope main body 100 according to the embodiments corresponds to an example of an endoscope.

Configuration Example of Processor Apparatus

The processor apparatus 200 includes an image input controller 202, an image processing unit 204, and a video output unit 206. The image input controller 202 acquires an electric signal transmitted from the endoscope main body 100 and corresponding to an optical image of an observation target.

On the basis of an imaging signal, which is the electric signal corresponding to the optical image of the observation target, the image processing unit 204 generates an endoscopic image of the observation target. Note that the term "image" herein may include the meaning of both the image itself and image data indicating the image. The image may include both a moving image and a still image. Note that the endoscopic image is denoted by reference numeral 38 and illustrated in FIG. 3.

The image processing unit 204 may correct image quality by applying digital signal processing such as white balance processing or shading correction processing on the imaging signal. The image processing unit 204 may add accessory information defined by the DICOM standard to the endoscopic image. Note that DICOM is an abbreviation for Digital Imaging and Communications in Medicine.

The video output unit 206 transmits, to the monitor 400, a display signal indicating an image generated by using the image processing unit 204. The monitor 400 displays an image of the observation target.

In response to an operation on the imaging button 144 illustrated in FIG. 1, in accordance with an imaging instruction signal transmitted from the endoscope main body 100, the processor apparatus 200 operates the image input controller 202, the image processing unit 204, and the like.

Upon acquiring a freeze instruction signal indicating still image capturing from the endoscope main body 100, the processor apparatus 200 generates a still image based on a frame image at the operation timing of the imaging button 144 by using the image processing unit 204. The processor apparatus 200 causes the monitor 400 to display the still image. Note that the frame image is denoted by reference numeral 38B and illustrated in FIG. 3. The still image is denoted by reference numeral 39 and illustrated in FIG. 3.

The processor apparatus 200 includes a communication control unit 205. The communication control unit 205 controls communication with an apparatus that is communicably connected via an in-hospital system, an in-hospital LAN, or the like. The communication control unit 205 may use a communication protocol conforming to the DICOM standard. Note that examples of the in-hospital system include HIS (Hospital Information System). LAN is an abbreviation for Local Area Network.

The processor apparatus 200 includes a storage unit 207. The storage unit 207 stores the endoscopic image captured by the endoscope main body 100. The storage unit 207 may also store various types of accessory information of the endoscopic image.

The processor apparatus 200 includes the operation unit 208. The operation unit 208 outputs an instruction signal in accordance with a user operation. A keyboard, a mouse, a joystick, and the like may be used as the operation unit 208.

A user input signal transmitted from the operation unit 208 is transmitted to a CPU 210. The CPU 210 acquires the user input signal transmitted from the operation unit 208 and performs control corresponding to the acquired user input signal. The operation unit 208 may include the above-described foot switch.

The CPU 210 acquires a user input signal transmitted from the handheld operation part 102 illustrated in FIG. 1, controls the endoscope main body 100 corresponding to the acquired user input signal, and controls the processor apparatus 200 and the light source apparatus 300.

The processor apparatus 200 includes a voice processing unit 209 and a speaker 209A. The voice processing unit 209 generates a voice signal indicating information to be notified as a voice. The speaker 209A converts the voice signal generated by the voice processing unit 209 into a voice. Examples of the voice output from the speaker 209A include a message, a voice guidance, an alarm sound, and the like.

The processor apparatus 200 includes the CPU 210, a ROM 211, and a RAM 212. Note that CPU is an abbreviation for Central Processing Unit, ROM is an abbreviation for Read Only Memory, and RAM is an abbreviation for Random Access Memory.

The CPU 210 functions as an overall control unit of the processor apparatus 200. The CPU 210 functions as a memory controller that controls the ROM 211 and the RAM 212. The ROM 211 stores various programs, control parameters, and the like to be used by the processor apparatus 200.

The RAM 212 is used as a temporal storage area of data in various types of processing and a processing area of calculation processing using the CPU 210. The RAM 212 may be used as a buffer memory when an endoscopic image is acquired.

The processor apparatus 200 performs various types of processing on the endoscopic image captured by the endoscope main body 100 and causes the monitor 400 to display the endoscopic image and various types of accessory information of the endoscopic image. The processor apparatus 200 stores the endoscopic image and the various types of accessory information of the endoscopic image.

That is, in an endoscope examination using the endoscope main body 100, the processor apparatus 200 displays the endoscopic image or the like on the monitor 400, outputs voice information by using the speaker 209A, and performs various types of processing on the endoscopic image.

By using a constituent element such as the image processing unit 204, the processor apparatus 200 may function as an image processing apparatus that performs predetermined processing on a medical image. Examples of the predetermined processing include region-of-interest detection processing, region-of-interest emphasis processing, region-of-interest classification processing, medical image differentiation processing, region-of-interest measurement processing, and the like.

Hardware Configuration of Processor Apparatus

A computer may be used as the processor apparatus 200. The computer may use the following hardware and execute a predetermined program to implement the functions of the processor apparatus 200. Note that the program is equivalent to software.

Various processors as a signal processing unit that performs signal processing may be used as the processor apparatus 200. Examples of the processor include a CPU and a GPU (Graphics Processing Unit). The CPU is a general-purpose processor that functions as a signal processing unit by executing a program. The GPU is a processor specialized in image processing. An electric circuit in which electric circuit elements such as semiconductor elements are combined may be used as hardware of the processor. Each control unit includes a ROM that stores a program and the like and a RAM that is a work area or the like of various calculations.

Two or more processors may be used as a single signal processing unit. The two or more processors may be processors of the same type or may be processors of different types. In addition, a single processor may be used as a plurality of signal processing units. Note that the processor apparatus 200 according to the embodiments corresponds to an example of an endoscope control apparatus.

Configuration Example of Light Source Apparatus

The light source apparatus 300 includes a light source 310, an aperture diaphragm 330, a condensing lens 340, and a light source control unit 350. The light source apparatus 300 causes observation light to enter the light guide 170. The light source 310 includes a red light source 310R, a green light source 310G, and a blue light source 310B. The red light source 310R, the green light source 310G, and the blue light source 310B emit red narrow-band light, green narrow-band light, and blue narrow-band light, respectively.

The light source 310 may generate illumination light obtained by combining red narrow-band light, green narrow-band light, and blue narrow-band light as appropriate. For example, the light source 310 may generate white light by combining red narrow-band light, green narrow-band light, and blue narrow-band light. The light source 310 may also generate narrow-band light by combining any two of red narrow-band light, green narrow-band light, and blue narrow-band light.

The light source 310 may generate narrow-band light by using any one of red narrow-band light, green narrow-band light, and blue narrow-band light. The light source 310 may emit white light or narrow-band light by selectively switching them. Note that the narrow-band light is equivalent to special light. The light source 310 may include an infrared light source that emits infrared light, an ultraviolet light source that emits ultraviolet light, and the like.

The light source 310 may employ a configuration of including a white light source that emits white light, a filter that transmits white light, and a filter that transmits narrow-band light. The light source 310 in this configuration may selectively emit any of white light or narrow-band light by switching the filter that transmits white light and the filter that transmits narrow-band light.

The filter that transmits narrow-band light may include a plurality of filters corresponding to different bands. The light source 310 may selectively emit a plurality of narrow-band light beams in different bands by selectively switching a plurality of filters corresponding to different bands.

The light source 310 may apply a type, a wavelength range, and the like in accordance with an observation target type, an observation purpose, and the like. Examples of the type of the light source 310 include a laser light source, a xenon light source, an LED light source, and the like. Note that LED is an abbreviation for Light-Emitting Diode.

Observation light emitted from the light source 310 when the light guide connector 108 is connected to the light source apparatus 300 reaches the incident end of the light guide 170 through the aperture diaphragm 330 and the condensing lens 340. The observation light is radiated on the observation target via the light guide 170, the illumination lens 123A, and the like.

On the basis of an instruction signal transmitted from the processor apparatus 200, the light source control unit 350 transmits a control signal to the light source 310 and the aperture diaphragm 330. The light source control unit 350 controls an illuminance of the observation light emitted from the light source 310, switching of the observation light, and ON/OFF state of the observation light, and the like.

Configuration Example of Image Processing Apparatus According to First Embodiment Outline When a physician who operates the endoscope main body 100 overlooks a region of interest such as a lesion in an observation image and advances an endoscope examination, they may notice the overlooking of the region of interest due to a trigger such as a voice notification or an emphasized image of the region of interest. When noticing the overlooking of the region of interest, the physician may search for the region of interest that is yet to be observed by operating the endoscope main body 100.

In response to the physician transmitting a user input signal indicating re-displaying of the unobserved region of interest, an image processing apparatus illustrated in this embodiment reads out an unobserved image that is a frame image including the unobserved region of interest and causes the monitor 400 illustrated in FIG. 1 to display the unobserved image. The unobserved image is displayed in a region that is different from an observation image display region in which an observation image is displayed. This enables the physician to compare the observation image and the unobserved image with each other and to search for the overlooked region of interest in the observation image.

The observation image is a real-time endoscopic image of an observation target displayed on the monitor 400 during an endoscope examination. The observation image may be a moving image or a still image. Note that the observation target described in the embodiments corresponds to an example of a subject. The monitor 400 described in the embodiments corresponds to an example of a display apparatus.

The real-time endoscopic image may include an image that is displayed on the monitor 400 after an elapse of a certain delay period from an imaging timing due to signal processing or the like. The image processing apparatus illustrated in this embodiment is equivalent to a medial image processing apparatus. The same applies to a second embodiment and a third embodiment.

Figure 3:
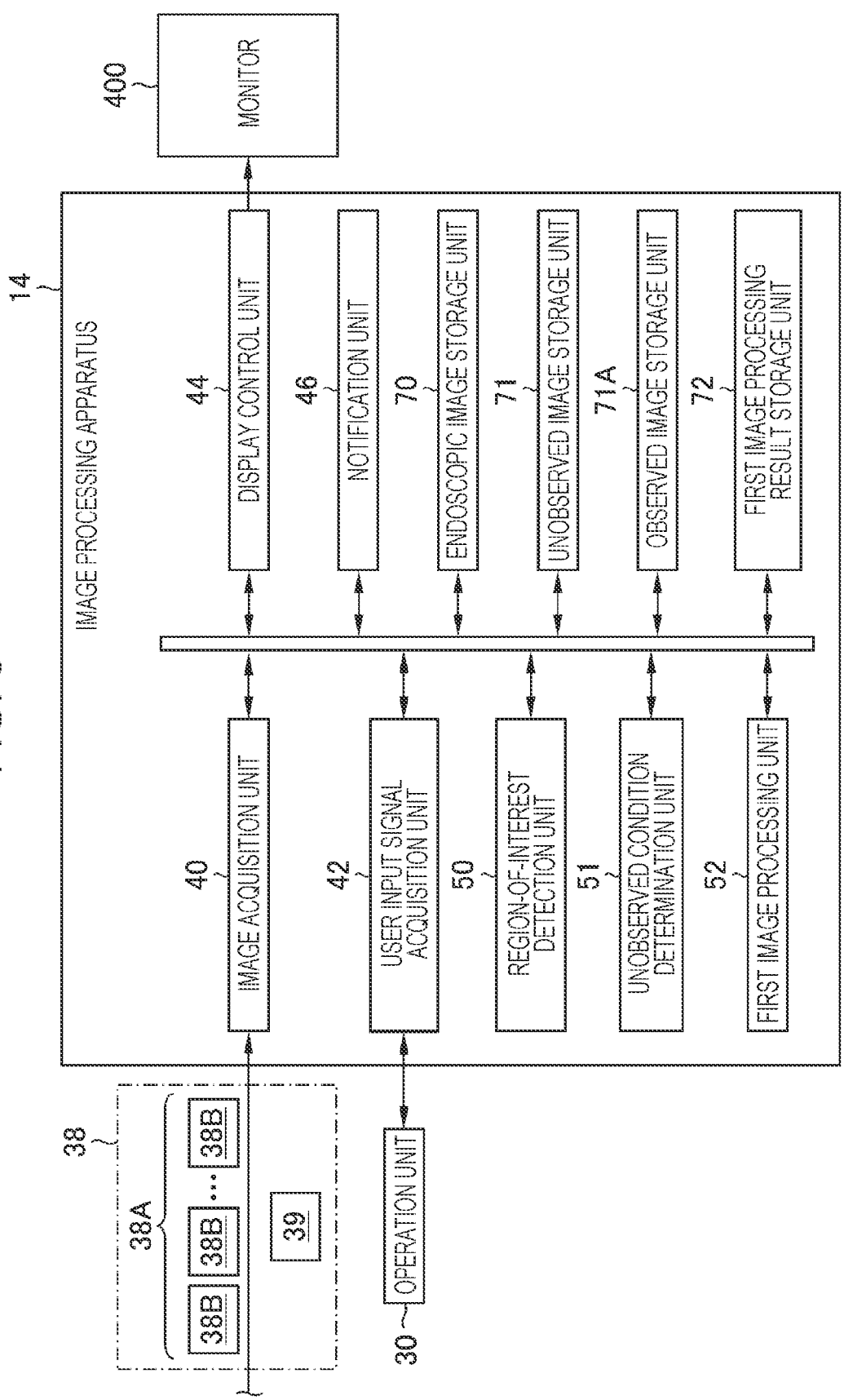
FIG. 3 is a functional block diagram of an image processing apparatus according to a first embodiment.

FIG. 3 is a functional block diagram of the image processing apparatus according to a first embodiment. An image processing apparatus 14 illustrated in FIG. 3 is implemented by using constituent elements such as the image processing unit 204 in the processor apparatus 200 illustrated in FIG. 2. The image processing apparatus 14 includes an image acquisition unit 40, a user input signal acquisition unit 42, a display control unit 44, and a notification unit 46.

The image processing apparatus 14 includes a region-of-interest detection unit 50, an unobserved condition determination unit 51, a first image processing unit 52, an endoscopic image storage unit 70, an unobserved image storage unit 71, an observed image storage unit 71A, and a first image processing result storage unit 72. Each unit will be described below.

Image Acquisition Unit

The image acquisition unit 40 acquires the endoscopic image 38 captured by the endoscope main body 100 illustrated in FIG. 1. Hereinafter, acquisition of the endoscopic image 38 may include acquisition of a moving image 38A, acquisition of a frame image 38B, and acquisition of a still image 39.

The image acquisition unit 40 stores the endoscopic image 38 in the endoscopic image storage unit 70. The image acquisition unit 40 may acquire the endoscopic image 38 from the processor apparatus 200 via a cable for transmitting a signal indicating the endoscopic image 38.

The image acquisition unit 40 may acquire the endoscopic image 38 from the processor apparatus 200 via an information storage medium such as a memory card. The image acquisition unit 40 may acquire the endoscopic image 38 via a communication network.

The image acquisition unit 40 may acquire the moving image 38A constituted by chronological frame images 38B. When a still image is captured while the moving image 38A is captured, the image acquisition unit 40 may acquire the still image 39. The image acquisition unit 40 corresponds to the image input controller 202 illustrated in FIG. 2.

User Input Signal Acquisition Unit

The user input signal acquisition unit 42 acquires a user input signal transmitted from an operation unit 30 in response to a user operation on the operation unit 30. The operation unit 30 illustrated in FIG. 3 may include the handheld operation part 102 illustrated in FIG. 1, the operation unit 208 illustrated in FIG. 2, a foot switch which is not illustrated, and the like.

The user input signal acquisition unit 42 may include a microphone that acquires the user's voice. That is, the user input signal acquisition unit 42 may acquire a user input signal based on the user's voice.

Note that the operation unit 30 described in the embodiments corresponds to an example of a user operation unit. The microphone described in the embodiments corresponds to an example of a voice acquisition unit that acquires the user's voice.

Display Control Unit

The display control unit 44 transmits, to the monitor 400, a display signal indicating the endoscopic image 38. The monitor 400 displays the endoscopic image 38 as an observation image. Upon detection of a region of interest from the endoscopic image 38, the display control unit 44 transmits, to the monitor 400, a display signal indicating a first image obtained by performing first image processing on the endoscopic image 38 by using the first image processing unit 52.

Upon the user input signal acquisition unit 42 acquiring a user input signal indicating displaying of an unobserved region of interest, the display control unit 44 transmits, to the monitor 400, a display signal indicating an unobserved image. The monitor 400 displays the unobserved image.

On the basis of a hiding condition of the unobserved image to be displayed on the monitor 400, the display control unit 44 hides the unobserved image. The display control unit 44 corresponds to the video output unit 206 illustrated in FIG. 2.

Note that the display control unit 44 described in the embodiments corresponds to an example of a display signal transmission unit that transmits, to the display apparatus, a first display signal indicating an observation image. The display signal indicating the endoscopic image 38 described in the embodiments corresponds to an example of the first display signal. A display signal indicating the unobserved image described in the embodiments corresponds to an example of a second display signal.

Notification Unit

Upon detection of a region of interest from a frame image 38B constituting the endoscopic image 38, the notification unit 46 issues a notification indicating that the region of interest is detected in the endoscopic image 38. The notification unit 46 may issue a voice notification using the speaker 209A illustrated in FIG. 2. The notification unit 46 may issue a notification of text information or the like by using the monitor 400.

Region-of-Interest Detection Unit

A learning machine such as CNN (Convolutional Neural Network) is used as the region-of-interest detection unit 50, and the region-of-interest detection unit 50 detects a region of interest from the frame image 38B acquired by the image acquisition unit 40. The region-of-interest detection unit 50 derives a feature quantity in the frame image 38B and determines whether a region of interest is present on the basis of the feature quantity.

A learning machine that has learned pairs of the frame image 38B and the region of interest in the frame image 38B as learning data is used as the region-of-interest detection unit 50. Examples of detection of the region of interest include detection of a lesion, detection of a specific organ, and the like.

Unobserved Condition Determination Unit

The unobserved condition determination unit 51 determines whether the frame image 38B in which the region of interest is detected satisfies a condition of the frame image 38B to be stored in the unobserved image storage unit 71. That is, the unobserved condition determination unit 51 determines whether the frame image 38B in which the region of interest is detected is an unobserved image.

When the region of interest is observed, a physician is considered to stop moving the imaging part 130 or slow down a moving speed of the imaging part 130. Thus, the number of frame images 38B including the same region of interest is larger when the region of interest is observed than when the region of interest is not observed.

Thus, a predetermined number of frame images 38B including the same region of interest is set in advance, and, when the number of frame images 38B including the same region of interest within a predetermined period is less than or equal to the predetermined number, the unobserved condition determination unit 51 determines that the frame image 38B is an unobserved image. The predetermined number may be determined in accordance with a frame rate of the imaging part 130 and the moving speed of the imaging part 130. Any given integer of greater than or equal to 1 may be used as the predetermined number. The frame images 38B including the same region of interest are continuous in many cases, but detection of the region of interest may be interrupted by flickering in screen. The predetermined number may be the number of continuous frame images 38B or may be the number of non-continuous frame images 38B.

Movement of the imaging part 130 indicates movement of the imaging part 130 along a movement path of the endoscope main body 100 in an endoscope examination. In addition, the movement velocity may include a concept of speed indicating an absolute value of the movement velocity.

When the region of interest is observed, an imaging direction of the imaging part 130 is considered to be changed a larger number of times than when the region of interest is not observed. Thus, on the basis of a change amount between frame images 38B, such as a change in a movement vector of the imaging part 130, the unobserved condition determination unit 51 may determine whether the frame image 38B is not observed by the physician. That is, when the change amount between frame images 38B is greater than or equal to a predetermined threshold value, the unobserved condition determination unit 51 may determine that the frame image 38B is an unobserved image. Other examples of the change amount between frame images 38B include a value of a cross-correlation function between frame images 38B and the like.

In addition, in many cases, the region of interest is observed in a center portion of the screen. Thus, when the region of interest remains in a peripheral portion of the screen and is out of frame, it may be determined that the frame image 38B is an unobserved image. In other words, when the same region of interest remains in a portion other than the center portion of the screen within a predetermined period, the unobserved condition determination unit 51 may determine that the frame image 38B is an unobserved image. Here, the center portion of the screen is a region including the center or the center of gravity of the screen and is a region not including an end of the screen. On the other hand, the peripheral portion of the screen is a region not including the center or the center of gravity of the screen and is a region including an end of the screen.

That is, when it is determined that observation is not performed on the basis of at least any of the number of frame images 38B including the same region of interest, the change amount between frame images 38B, or the position of the region of interest on the screen, the unobserved condition determination unit 51 may determine that the frame image 38B is an unobserved image.

When the frame image 38B in which the region of interest is detected satisfies the condition of the unobserved image to be stored in the unobserved image storage unit 71, the unobserved condition determination unit 51 stores the frame image 38B in the unobserved image storage unit 71 as the unobserved image.

On the other hand, when the frame image 38B in which the region of interest is detected does not satisfy the condition of the unobserved image to be stored in the unobserved image storage unit 71, the unobserved condition determination unit 51 stores the frame image 38B in the observed image storage unit 71A as an observed image.

First Image Processing Unit

Upon detection of the region of interest from the frame image 38B constituting the endoscopic image 38, the first image processing unit 52 performs first image processing on the frame image 38B including the region of interest. The endoscopic image 38 and the frame image 38B including the region of interest herein corresponds to the above-described observation image.

Region-of-interest emphasis processing may be used as the first image processing. The first image processing unit 52 generates an emphasis image emphasizing the region of interest detected from the frame image 38B. Examples of the emphasis image include a bounding box to be superimposed on the region of interest, a predetermined color and pattern to be added to the region of interest, and the like.

The first image processing unit 52 identifies the position of the region of interest and determines the position of the emphasis image in accordance with the position of the region of interest. The first image processing unit 52 identifies the size of the region of interest and determines the size of the emphasis image in accordance with the size of the region of interest.

The first image processing unit 52 stores a processing result of the first image processing in the first image processing result storage unit 72. The first image processing result storage unit 72 may store a first image obtained by adding the emphasis image to the frame image 38B in which the region of interest is detected. The first image processing result storage unit 72 may store a combination of the frame image 38B including the region of interest and information of the emphasis image associated with the frame image 38B including the region of interest. That is, the first image processing unit 52 may store a file of the frame image 38B and a file of the emphasis image as different files.

By using the display control unit 44, the first image processing unit 52 causes the monitor 400 to display the frame image 38B on which the emphasis image is superimposed as the observation image. The notification unit 46 may issue a notification indicating that the region of interest is detected in the endoscopic image 38 by using the frame image 38B on which the emphasis image is superimposed.

Endoscopic Image Storage Unit

The endoscopic image storage unit 70 stores the endoscopic image 38 acquired by the image acquisition unit 40. When a still image is captured, the endoscopic image storage unit 70 stores the still image 39 generated in capturing the still image.

Unobserved Image Storage Unit

The unobserved image storage unit 71 stores the unobserved image. Upon acquisition of the user input signal indicating displaying of the unobserved region of interest, the display control unit 44 reads out the unobserved image stored in the unobserved image storage unit 71.

When a new unobserved image is generated while the unobserved image is stored, the unobserved image storage unit 71 may store the new unobserved image instead of the already stored unobserved image.

The unobserved image storage unit 71 may determine the number of unobserved images to be stored. The unobserved image storage unit 71 may also determine an unobserved image storing period. That is, the unobserved image storage unit 71 may store unobserved images that are likely to be re-displayed and may delete unobserved images that are unlikely to be re-displayed. Note that the unobserved images are omitted from the illustrated in FIG. 3.

Observed Image Storage Unit

The observed image storage unit 71A stores the observed image. Upon acquisition of the user input signal indicating displaying of the region of interest that is observed, the display control unit 44 reads out the observed image stored in the observed image storage unit 71A.

First Image Processing Result Storage Unit

The first image processing result storage unit 72 stores the processing result of the first image processing performed by the first image processing unit 52. The first image, or a combination of the frame image 38B and information of the region of interest associated with the frame image 38B, may be used as the result of the first image processing.

Each of the endoscopic image storage unit 70, the unobserved image storage unit 71, the observed image storage unit 71A, and the first image processing result storage unit 72 may use one or more storage elements. That is, the image processing apparatus 14 may include four storage elements corresponding to the endoscopic image storage unit 70, the unobserved image storage unit 71, the observed image storage unit 71A, and the first image processing result storage unit 72, respectively.

Any two to four of the endoscopic image storage unit 70, the unobserved image storage unit 71, the observed image storage unit 71A, and the first image processing result storage unit 72 may be constituted by using a single storage element. For example, the endoscopic image storage unit 70, the unobserved image storage unit 71, and the observed image storage unit 71A may be constituted by using a single storage element.

Procedure of Image Processing Method According to First Embodiment

Figure 4:
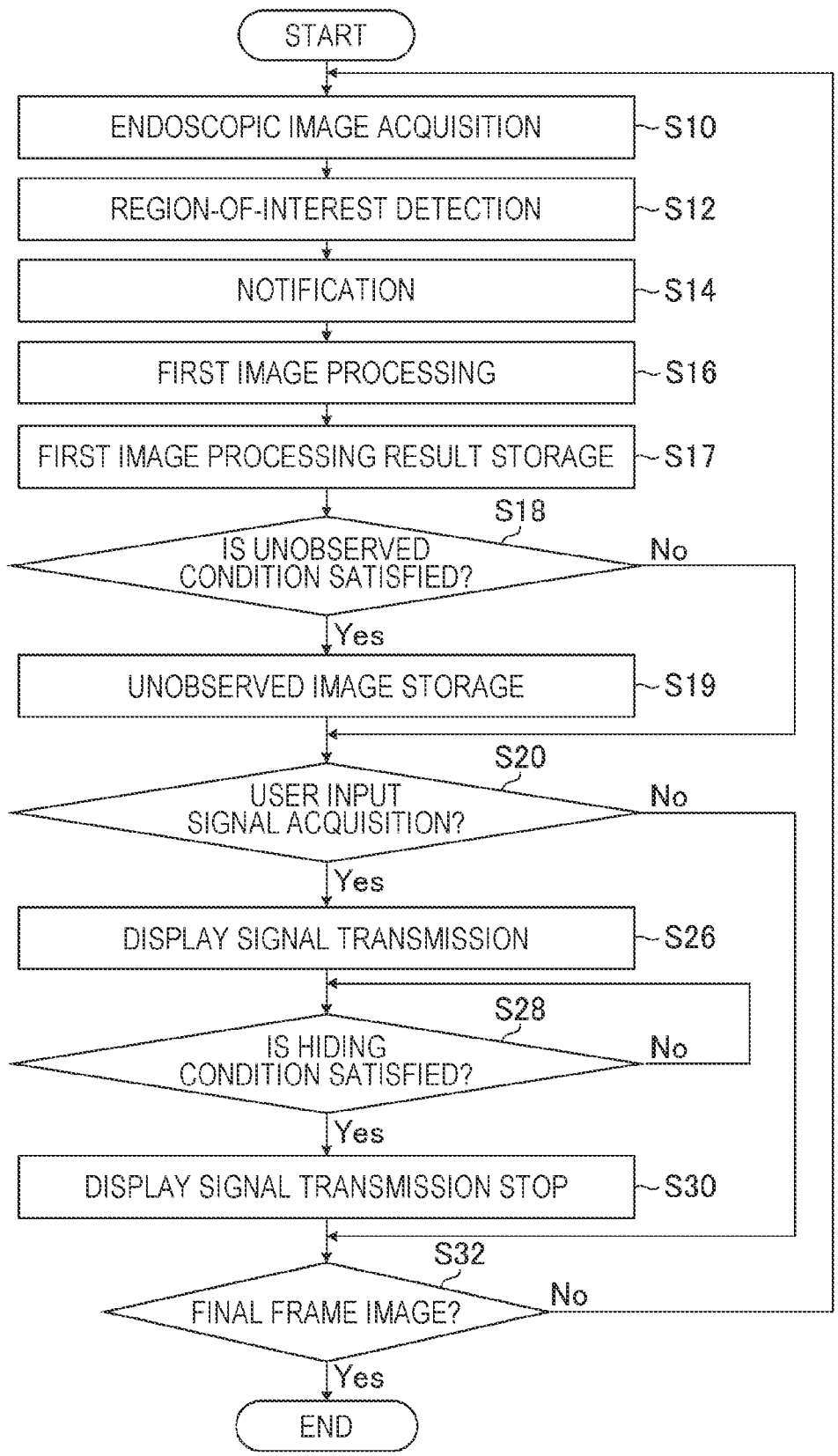
FIG. 4 is a flowchart illustrating a procedure of an image processing method according to the first embodiment.

FIG. 4 is a flowchart illustrating a procedure of an image processing method according to the first embodiment. Note that the image processing method illustrated in this embodiment is equivalent to a medical image processing method and the like. The same applies to a second embodiment and a third embodiment.

In an endoscopic image acquisition step S10, the image acquisition unit 40 illustrated in FIG. 3 acquires an endoscopic image 38. In the endoscopic image acquisition step S10, the image acquisition unit 40 stores the endoscopic image 38 in the endoscopic image storage unit 70. After the endoscopic image acquisition step S10, the process advances to a region-of-interest detection step S12.

In the region-of-interest detection step S12, the region-of-interest detection unit 50 detects a region of interest from each of frame images 38B constituting the endoscopic image 38. In the region-of-interest detection step S12, the region-of-interest detection unit 50 may detect the region of interest from all the frame images 38B of the moving image 38A or may detect the region of interest from frame images 38B at predetermined intervals. After the region-of-interest detection step S12, the process advances to a notification step S14.

In the notification step S14, the notification unit 46 issues a notification indicating that the region of interest is detected in a frame image 38B. A notification stopping step of stopping the notification may also be performed. After the notification step S14, the process advances to a first image processing step S16.

In the first image processing step S16, the first image processing unit 52 performs first image processing on the frame image 38B in which the region of interest is detected. After the first image processing step S16, the process advances to a first image processing result storage step S17. After the first image processing step S16 is performed, the notification step S14 may also be performed.

In the first image processing result storage step S17, the first image processing unit 52 stores a processing result of the first image processing in the first image processing result storage unit 72. After the first image processing result storage step S17, the process advances to an unobserved condition determination step S18. After first image processing result storage step S17, a display step of displaying a first image may also be performed. In addition, the first image processing step S16 and the first image processing result storage step S17 may be skipped.

In the unobserved condition determination step S18, the unobserved condition determination unit 51 determines whether the frame image 38B in which the region of interest is detected satisfies an unobserved condition. That is, in the unobserved condition determination step S18, the unobserved condition determination unit 51 determines whether the frame image 38B in which the region of interest is detected is an unobserved image.

A case where the unobserved condition determination unit 51 determines that the unobserved condition is not satisfied in the unobserved condition determination step S18 corresponds to No determination. In a case of No determination, the process advances to a user input signal acquisition determination step S20.

On the other hand, a case where the unobserved condition determination unit 51 determines that the unobserved condition is satisfied in the unobserved condition determination step S18 corresponds to Yes determination. In a case of Yes determination, the process advances to an unobserved image storage step S19.

In the unobserved image storage step S19, the unobserved condition determination unit 51 stores the unobserved image in the unobserved image storage unit 71. After the unobserved image storage step S19, the process advances to the user input signal acquisition determination step S20. Before or after the unobserved image storage step S19, or in parallel to the unobserved image storage step S19, an observed image storage step of storing an observed image in the observed image storage unit 71A may also be performed.

In the user input signal acquisition determination step S20, the user input signal acquisition unit 42 determines whether a user input signal indicating displaying of an unobserved region of interest is acquired. A case where the user input signal acquisition unit 42 determines that the user input signal indicating displaying of the unobserved region of interest is not acquired in the user input signal acquisition determination step S20 corresponds to No determination. In a case of No determination, the process advances to a final frame image determination step S32.

On the other hand, a case where the user input signal acquisition unit 42 determines that the user input signal indicating displaying of the unobserved region of interest is acquired in the user input signal acquisition determination step S20 corresponds to Yes determination. In a case of Yes determination, the process advances to a display signal transmission step S26. Note that the user input signal acquisition determination step S20 is an example of a user input signal acquisition step.

In the display signal transmission step S26, the display control unit 44 transmits, to the monitor 400, a display signal indicating that observation is yet to be performed. The monitor 400 displays that observation is yet to be performed. After the display signal transmission step S26, the process advances to a hiding condition determination step S28.

In the hiding condition determination step S28, the display control unit 44 determines whether a hiding condition of the unobserved image displayed on the monitor 400 is satisfied. A case where the display control unit 44 determines that the hiding condition of the unobserved image is not satisfied in the hiding condition determination step S28 corresponds to No determination. In a case of No determination, the hiding condition determination step S28 is continuously performed until Yes determination in the hiding condition determination step S28.

On the other hand, a case where the display control unit 44 determines that the hiding condition of the unobserved image is satisfied in the hiding condition determination step S28 corresponds to Yes determination. In a case of Yes determination, the process advances to a display signal transmission stopping step S30. Note that details of the hiding condition of the unobserved image will be described later.

In the display signal transmission stopping step S30, the display control unit 44 stops transmitting the display signal indicating the unobserved image displayed on the monitor 400. That is, in the display signal transmission stopping step S30, the display control unit 44 hides the unobserved image. After the display signal transmission stopping step S30, the process advances to the final frame image determination step S32.

In the final frame image determination step S32, the region-of-interest detection unit 50 determines whether region-of-interest detection processing is performed on a final frame image 38B in the endoscopic image 38 acquired by the image acquisition unit 40.

A case where the region-of-interest detection unit 50 determines that the region-of-interest detection processing is not performed on the final frame image 38B in the final frame image determination step S32 corresponds to No determination. In a case of No determination, the process advances to the endoscopic image acquisition step S10, and the steps from the endoscopic image acquisition step S10 to the final frame image determination step S32 are repeatedly performed until Yes determination in the final frame image determination step S32.

On the other hand, a case where the region-of-interest detection unit 50 determines that the region-of-interest detection processing is performed on the final frame image 38B in the final frame image determination step S32 corresponds to Yes determination. In a case of Yes determination, the image processing apparatus 14 ends the image processing method.

Display Examples of Endoscopic Image

Figure 5:
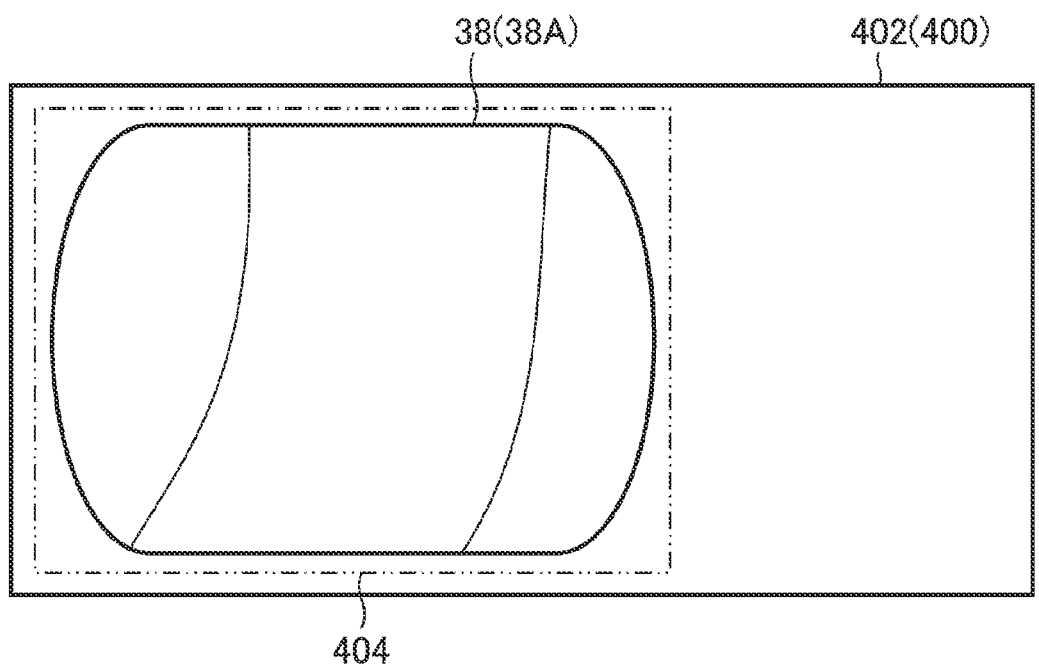
FIG. 5 schematically illustrates an observation image.

FIG. 5 schematically illustrates an observation image. FIG. 5 schematically illustrates an observation image of a large intestine as an endoscopic image 38. The same applies to FIGS. 6 to 8, FIGS. 11 to 13, and FIG. 16. If a region of interest is not detected from the endoscopic image 38, the endoscopic image 38 is displayed in real time as the observation image in an observation image display region 404 on a screen 402 of the monitor 400.

That is, on the screen 402 of the monitor 400 illustrated in FIG. 5, a moving image 38A of the endoscopic image 38 during an endoscope examination is displayed in real time as the observation image. The observation image illustrated in FIG. 5 illustrates a case where a region of interest is not detected from a frame image 38B constituting the endoscopic image 38.

Figure 6:
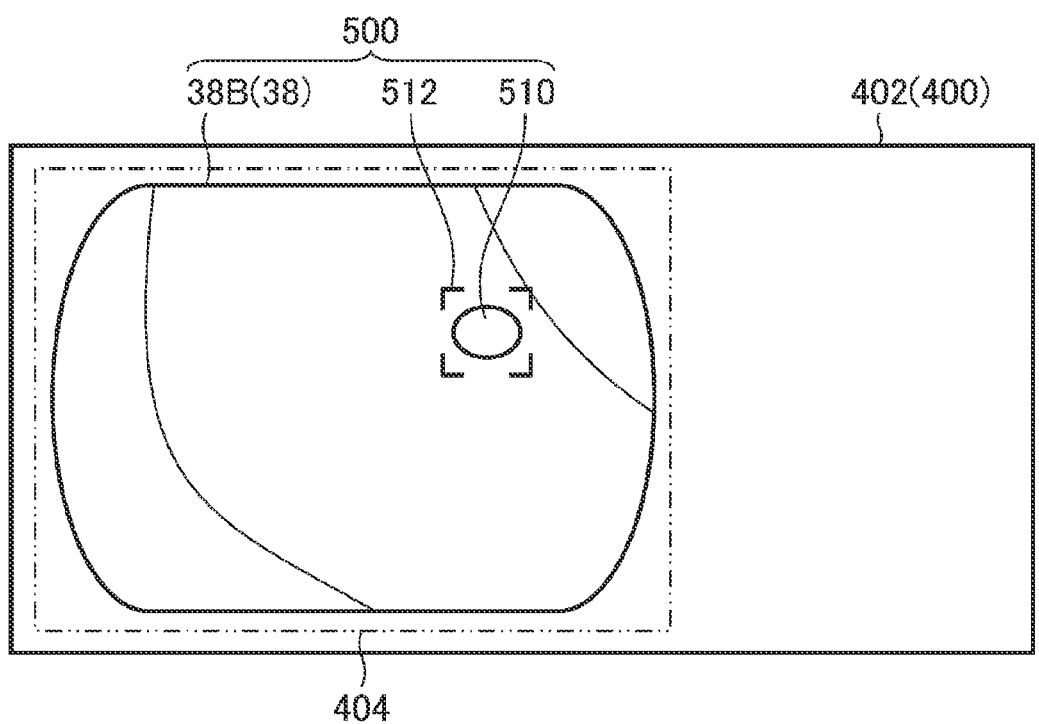
FIG. 6 schematically illustrates a first image.

FIG. 6 schematically illustrates a first image. If a region of interest 510 is detected from a frame image 38B constituting the endoscopic image 38, the first image processing unit 52 illustrated in FIG. 3 performs first image processing on the frame image 38B in accordance with a detection result of the region of interest 510.

The screen 402 of the monitor 400 illustrated in FIG. 6 displays a first image 500 to which emphasis processing of the region of interest 510 is applied as the first image processing and in which a bounding box 512 surrounding the region of interest 510 is superimposed on the frame image 38B in which the region of interest 510 is detected.

If a plurality of first images 500 are generated for the same region of interest 510, any given one or more first images 500 may be stored. FIG. 6 illustrates a first image 500 corresponding to a frame image 38B at a given timing.

FIG. 7 schematically illustrates a screen in a case where a user input signal indicating displaying of an unobserved region of interest is acquired. A physician who grasps detection of the region of interest 510 by a notification of detection of the region of interest 510 may wish to display the overlooked region of interest 510 on the screen 402.

Upon the user input signal acquisition unit 42 illustrated in FIG. 3 acquiring the user input signal indicating displaying of the unobserved region of interest, the display control unit 44 reads out an unobserved image from the unobserved image storage unit 71, and causes a read out unobserved image 39A to be displayed in an unobserved image display region 406 of the screen 402. The display control unit 44 causes the endoscopic image 38 to be displayed in real time in the observation image display region 404 of the screen 402. Thus, a physician observes the endoscopic image 38 and may find the overlooked region of interest 510 by using the unobserved image 39A displayed in the unobserved image display region 406.

FIG. 7 illustrates a second image 520 in which the region of interest 510 and the bounding box 512 are superimposed on the unobserved image 39A. That is, the unobserved image display region 406 may display the unprocessed unobserved image 39A or may use the second image 520 obtained by performing second image processing on the unobserved image 39A. Note that details of the second image processing will be described later.

Hiding Condition in Unobserved Image Display Region

FIG. 8 schematically illustrates an unobserved image display region that is hidden. On the screen 402 illustrated in FIG. 8, the second image 520 that has been displayed in the unobserved image display region 406 is hidden. FIG. 8 illustrates the second image 520 that is hidden by using the dotted line.

An elapse of a predetermined period from a display start timing of the second image 520 may be used as a hiding condition of the second image 520. That is, the image processing apparatus 14 includes a timer. The timer measures a period from the display start timing of the second image 520. On the basis of a measurement value of the timer, the display control unit 44 may hide the second image 520. Note that the timer is omitted from the illustration.

Note that the display control unit 44 described in the embodiments corresponds to an example of a display signal transmission unit that stops transmitting a second display signal after an elapse of a predetermined period from a transmission timing of the second display signal.

Viewing of the same region of interest 510 as the region of interest 510 in the second image 520 may be used as the hiding condition of the second image 520. The region-of-interest detection unit 50 illustrated in FIG. 3 determines sameness of the region of interest 510 in the second image 520 and the region of interest 510 detected from the endoscopic image 38.

The region-of-interest detection unit 50 illustrated in FIG. 3 may compare a feature quantity of the region of interest 510 in the second image 520 and a feature quantity of the region of interest 510 detected from the endoscopic image 38 and determine the sameness of the regions of interest 510 on the basis of a comparison result. The region-of-interest detection unit 50 may use a pixel value, the number of pixels, shape information, or the like as the feature quantity of the region of interest 510.

If a determination result indicating that the region of interest 510 in the second image 520 and the region of interest 510 in the endoscopic image 38 are the same is obtained, the display control unit 44 hides the second image 520 that has been displayed in the unobserved image display region 406.

If it is determined that the region of interest 510 in the second image 520 and the region of interest 510 in the endoscopic image 38 are the same, the notification unit 46 illustrated in FIG. 3 may notify the determination result by using a voice notification, a text notification, or the like. The hiding condition in the unobserved image display region 406 may be used for the unobserved image 39A when the unobserved image 39A is displayed in the unobserved image display region 406.

Effects of First Embodiment

The image processing apparatus 14 and the image processing method according to the first embodiment can obtain the following effects.

[1]

The region-of-interest detection unit 50 detects the region of interest 510 from the frame image 38B constituting the moving image 38A of the endoscopic image 38. The unobserved image storage unit 71 stores the unobserved image 39A including the region of interest 510 that is unobserved, from the endoscopic image 38 in which the region of interest 510 is detected. This enables a physician to search for the region of interest 510 using the unobserved image 39A or the like when noticing that the region of interest 510 has been overlooked by being notified that the region of interest 510 is detected.

[2]

Upon acquisition of a user input signal indicating displaying of the region of interest 510 that is unobserved, the display control unit 44 reads out the unobserved image 39A stored in the unobserved image storage unit 71 and causes the monitor 400 to display the read out unobserved image 39A or the second image 520. This enables the physician to search for the region of interest 510 using the unobserved image 39A or the like displayed on the monitor 400 when noticing that the region of interest 510 has been overlooked by being notified that the region of interest 510 is detected.

[3]

The display control unit 44 causes the unobserved image 39A or the second image 520 to be displayed in the unobserved image display region 406 that is a different region from the observation image display region 404. This enables the physician to search for the region of interest 510 in the observation image easily.

[4]

Upon acquisition of a user input signal indicating hiding of the unobserved image 39A or the second image 520, the display control unit 44 hides the unobserved image 39A or the second image 520. This may cause the unobserved image 39A, which may possibly disturb observation, to be hidden when the region of interest 510 that is a search target is found.

[5]

After an elapse of a predetermined period from a display start timing of the unobserved image 39A or the second image 520, the display control unit 44 hides the unobserved image 39A or the second image 520. This may cause the unobserved image 39A or the second image 520, which may possibly disturb observation, to be hidden automatically.

[6]

The user input signal acquisition unit 42 acquires a user input signal transmitted from an operation unit or a user input signal corresponding to a user's voice using a microphone. Thus, the user input signal acquisition unit 42 may apply various types of user input signals.

[7]

The first image processing unit 52 performs first image processing on the frame image 38B in which the region of interest 510 is detected. The display control unit 44 causes the first image 500 indicating a process result of the first image processing unit 52 to be displayed in the observation image display region 404. This may enable the physician to view detection of the region of interest in the observation image.

[8]

The first image processing unit 52 generates the second image 520 obtained by performing second image processing on the unobserved image 39A, the second image processing being processing to which image processing with the same details as those of the first image processing is applied. The display control unit 44 causes the second image 520 to be displayed in the unobserved image display region 406. This may increase the visibility of the region of interest 510 in the second image 520.

Modification Example of Image Processing Apparatus and Method According to First Embodiment Although the image processing apparatus and method according to the first embodiment causes the monitor 400 to display the unobserved image 39A on the basis of a user input signal, the monitor 400 may be caused to display the unobserved image 39A on the basis of generation of the unobserved image 39A.

According to the modification example, the monitor 400 may automatically display the unobserved image 39A upon generation of the unobserved image 39A.

Image Processing Apparatus According to Second Embodiment

Figure 9:
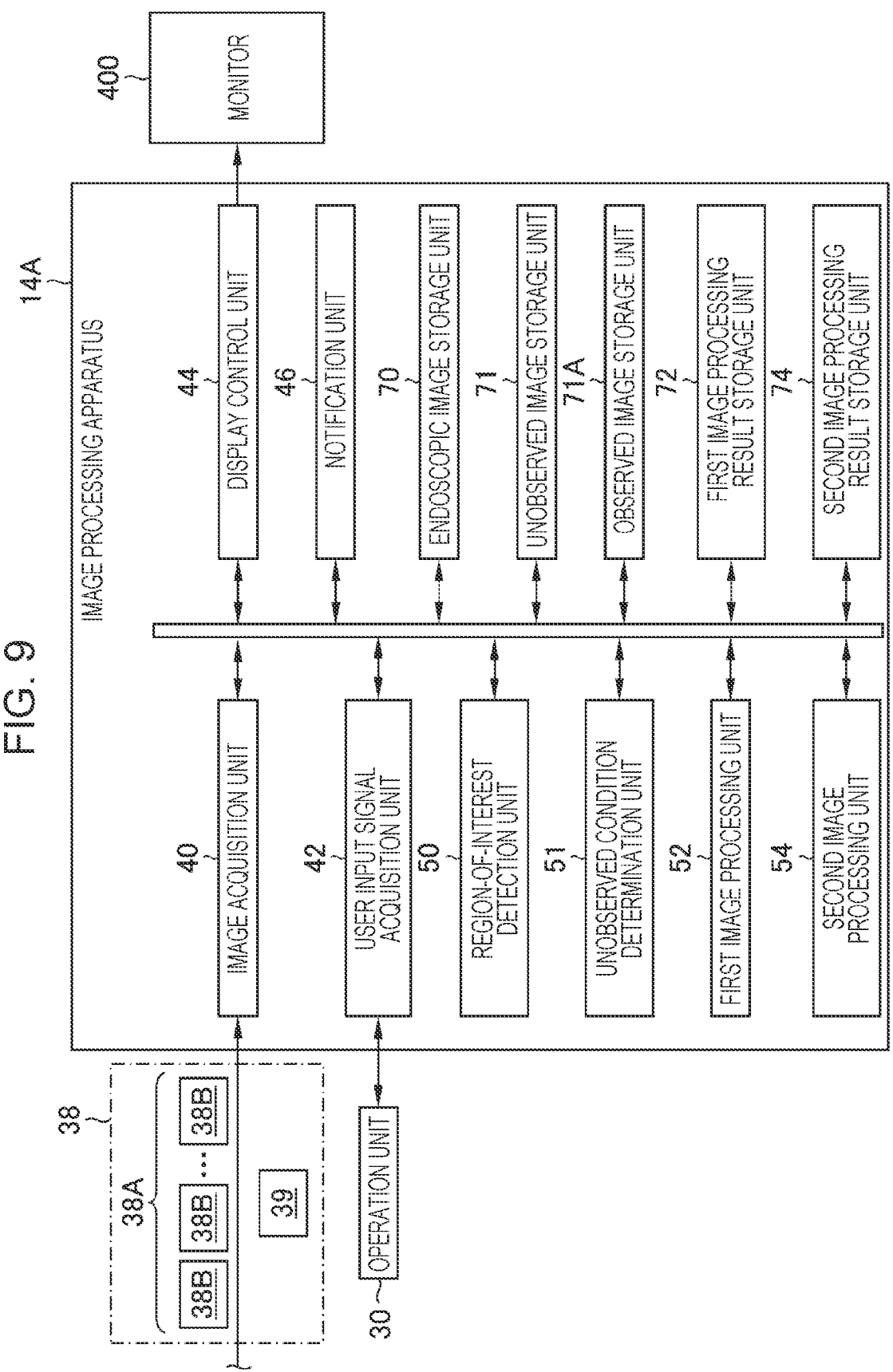
FIG. 9 is a functional block diagram of an image processing apparatus according to a second embodiment.

Next, an image processing apparatus according to the second embodiment will be described. FIG. 9 is a functional block diagram of the image processing apparatus according to the second embodiment. An image processing apparatus 14 image processing apparatus 14A illustrated in FIG. 9 is obtained by adding a second image processing unit 54 and a second image processing result storage unit 74 to the image processing apparatus 14 illustrated in FIG. 3.

Second Image Processing Unit

The second image processing unit 54 performs second image processing on the unobserved image 39A illustrated in FIG. 7. That is, when the unobserved image 39A is displayed in the unobserved image display region 406, the second image processing unit 54 changes a display manner of the second image 520 from a display manner of the first image 500 to be displayed in the observation image display region 404.

Emphasis processing of increasing an emphasis degree compared with the first image 500 may be applied as the second image processing. Batch display of a plurality of different second images 520 may be applied as the second image processing. Processing of selecting one of the plurality of different second images 520 may be applied as the second image processing.

The second image processing unit 54 stores a processing result of the second image processing in the second image processing result storage unit 74. The second image 520 may be used as the processing result of the second image processing. A combination of the unobserved image 39A and information indicating the processing result of the second image processing on the unobserved image 39A may be used as the processing result of the second image processing.

Second Image Processing Result Storage Unit

The second image processing result storage unit 74 stores the processing result of the second image processing performed by the second image processing unit 54. The second image processing result storage unit 74 may store the processing result of the second image processing selected from a plurality of processing results of the second image processing.

Procedure of Image Processing Method According to Second Embodiment

Figure 10:
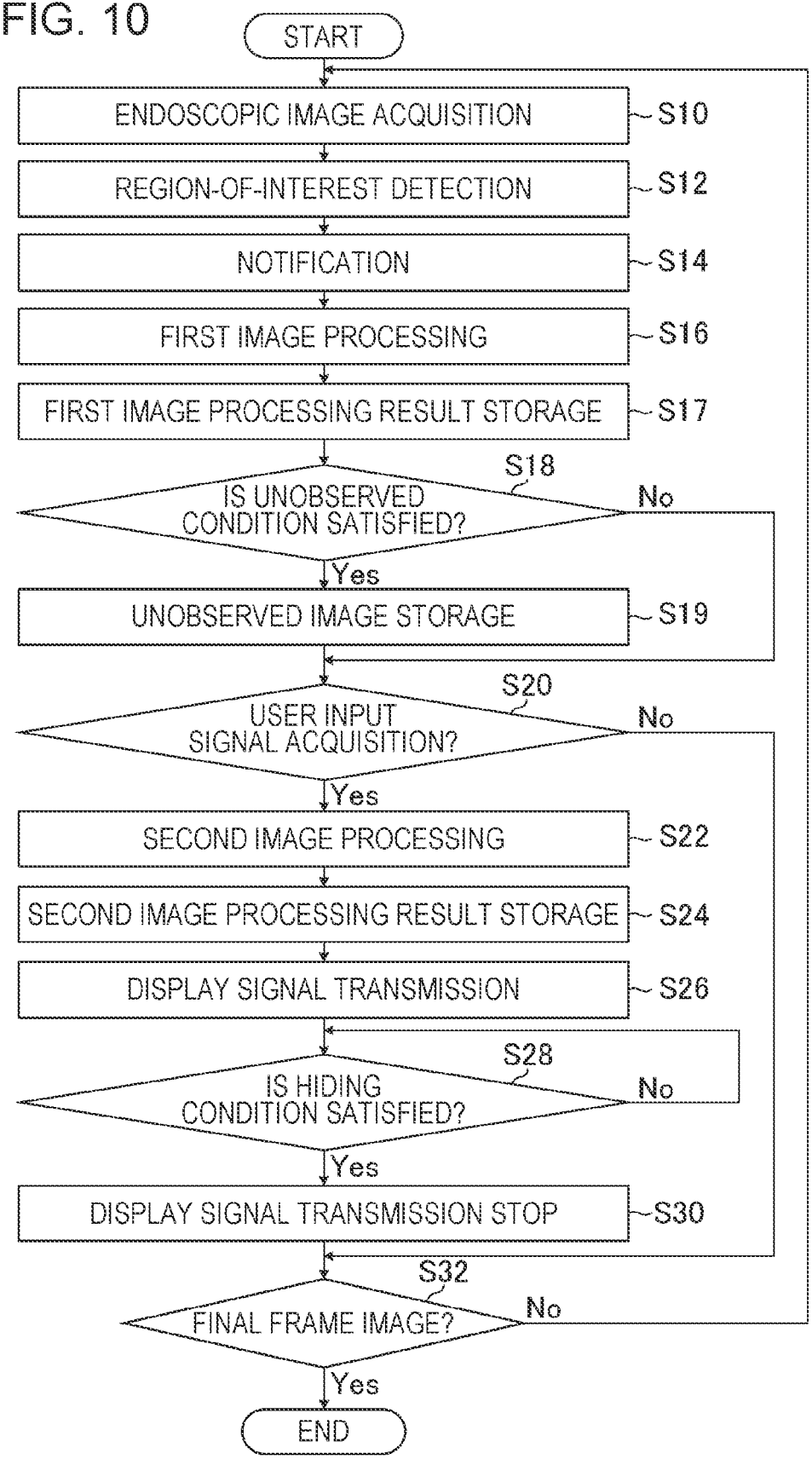
FIG. 10 is a flowchart illustrating a procedure of an image processing method according to the second embodiment.

FIG. 10 is a flowchart illustrating a procedure of an image processing method according to the second embodiment. The flowchart illustrated in FIG. 10 is obtained by adding a second image processing step S22 and a second image processing result storage step S24 to the flowchart illustrated in FIG. 4.

The steps from the endoscopic image acquisition step S10 to the user input signal acquisition determination step S20 illustrated in FIG. 10 are the same as the steps from the endoscopic image acquisition step S10 to the user input signal acquisition determination step S20 illustrated in FIG. 4. In a case of Yes determination in the user input signal acquisition determination step S20, the process advances to the second image processing step S22.

In the second image processing step S22, the second image processing unit 54 illustrated in FIG. 9 performs second image processing on the unobserved image 39A. After the second image processing step S22, the process advances to the second image processing result storage step S24.

In the second image processing result storage step S24, the second image processing unit 54 stores a result of the second image processing in the second image processing result storage unit 74. After the second image processing result storage step S24, the process advances to the display signal transmission step S26. Note that the second image processing step S22 and the second image processing result storage step S24 may be performed between the first image processing result storage step S17 and the unobserved condition determination step S18.

Specific Examples of Second Image Processing

Figure 11:
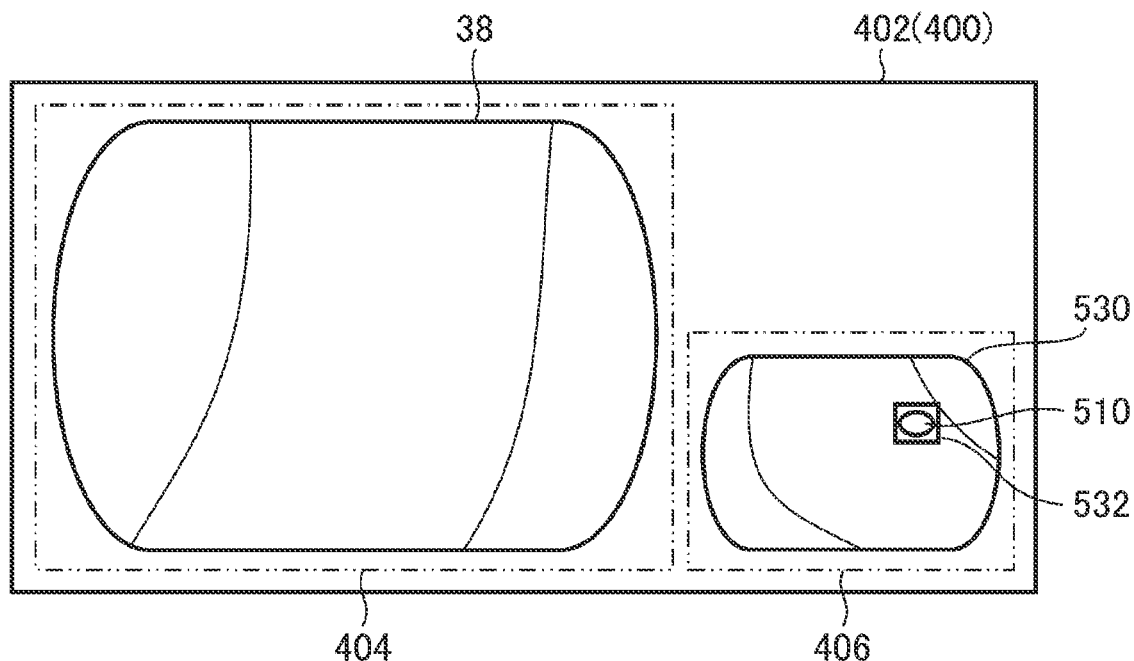
FIG. 11 schematically illustrates a second image to which image processing of increasing an emphasis degree is to be applied.

FIG. 11 schematically illustrates a second image to which image processing of increasing an emphasis degree is to be applied. In the unobserved image display region 406 illustrated in FIG. 11, a second image 530 in which the emphasis degree is increased compared with an emphasis degree of the emphasis processing in the first image 500 illustrated in FIG. 8 is displayed.

A bounding box 532 by which the emphasis degree of the region of interest 510 is increased compared with the bounding box 512 illustrated in FIG. 6 is applied in the second image 530. Compared with the bounding box 512 applied in the first image 500, as for the bounding box 532, the type of the frame line is changed from a broken line to a solid line, the width of the frame line is thickened, and the color of the frame line is outstanding color such as red.

The processing of increasing the emphasis degree is not limited to the configuration illustrated in FIG. 11. For example, at least any of the type of the frame line, the line width of the frame line, or the color of the frame line may be changed from the bounding box 512 illustrated in FIG. 6.

On the screen 402 on which the second image 530 is displayed in the unobserved image display region 406, the endoscopic image 38 is displayed in real time in the observation image display region 404. When noticing a notification indicating that the region of interest 510 is detected, a physician may refer to the second image 530 to search for the region of interest 510 by operating the endoscope main body 100 illustrated in FIG. 1.

The second image 530 illustrated in FIG. 11 may increase the visibility of the region of interest 510 compared with the unobserved image 39A displayed in the unobserved image display region 406 illustrated in FIG. 7.

Figure 12:
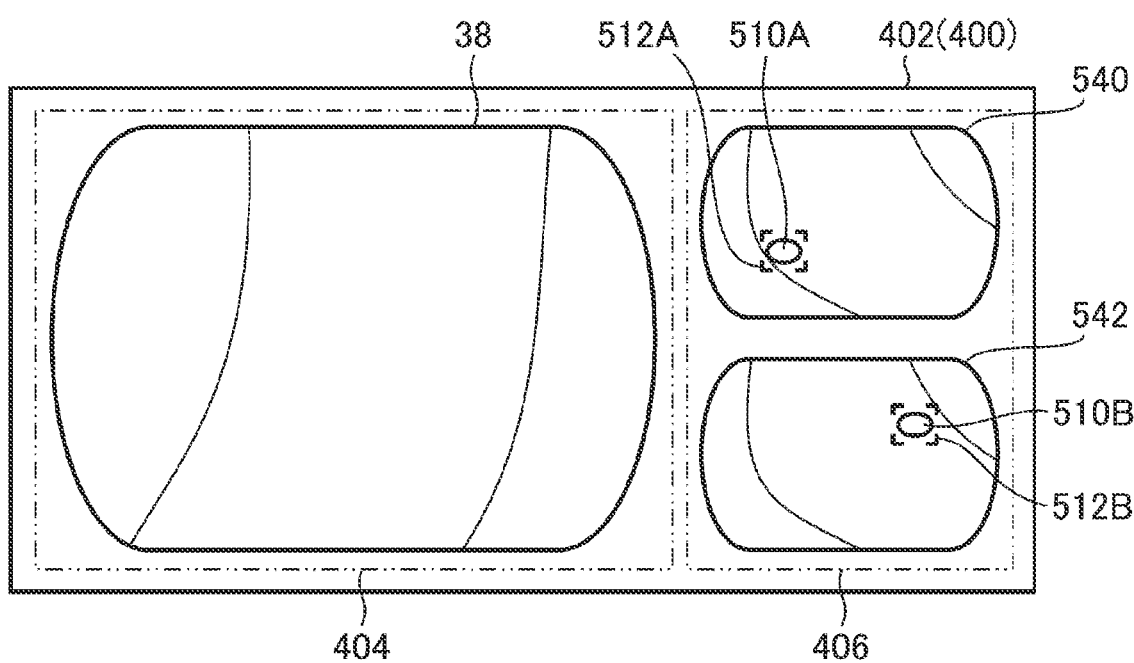
FIG. 12 schematically illustrates a configuration of displaying a plurality of second images.

FIG. 12 schematically illustrates a configuration of displaying a plurality of second images. A second image 540 and a second image 542 illustrated in FIG. 12 correspond to unobserved images 39A generated at different timings from each other.

Figure 13:
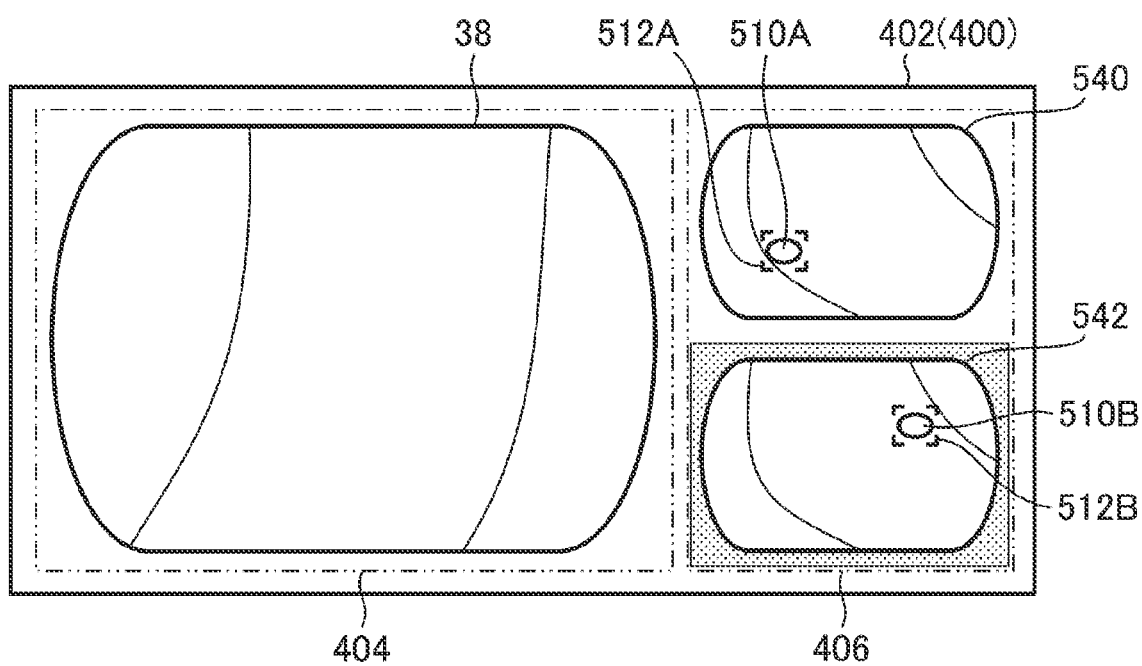
FIG. 13 schematically illustrates selection of a second image in the configuration of displaying a plurality of second images.

A bounding box 512A is superimposed on a region of interest 510A in the second image 540, and a bounding box 512B is superimposed on a region of interest 510B in the second image 542. When a plurality of second images including the second image 540 and the like are displayed, each of the second image 540 and the like may be displayed in a time-division manner FIG. 13 schematically illustrates selection of a second image in the configuration of displaying a plurality of second images. On the screen 402 illustrated in FIG. 13, the second image 542 that is selected from between the second image 540 and the second image 542 is highlighted. That is, upon acquisition of a user input signal indicating selection from the second image 540 and the like, the second image processing unit 54 highlights the selected second image 542 on the basis of the user input signal.

On the screen 402 illustrated in FIG. 13, in accordance with the selection of the second image 542, the unselected second image 540 may be hidden. In response to hiding of the unselected second image 540, highlighting of the second image 542 may be stopped. Note that the user input signal acquisition unit 42 illustrated in FIG. 9 corresponds to an example of a selection unit.

Although a configuration of displaying two second images including the second image 540 and the like is illustrated in FIGS. 12 and 13, three or more second images may be displayed. When a plurality of second images including the second image 540 and the like are displayed, information indicating the respective acquisition timings may be added. In a preferred embodiment, the plurality of second images including the second image 540 and the like are disposed in an order of the respective acquisition timings. In addition, in the selection from among the options of the plurality of second images including the second image 540 and the like, two or more second images may be selected.

According to the configuration illustrated in FIGS. 12 and 13, a plurality of second images including the second image 540 and the like may be used as a plurality of search candidates. In addition, one or more search targets may be selected from among the plurality of search candidates.

Other examples of the second image processing illustrated in FIGS. 11 to 13 include changing of at least any of a hue, a brightness, or a saturation of the region of interest 510 from the first image 500. Still other examples of the second image processing include resolution conversion such as resolution decrease and resolution increase. Still other examples of the second image processing include displaying of various types of information related to the second image 530 or the like, such as displaying of information related to a storing timing of the unobserved image 39A and displaying of a differentiation result of the region of interest 510 in the unobserved image 39A. A text and voice may be used in the displaying of various types of information.

Effects of Second Embodiment

The image processing apparatus 14A and the image processing method according to the second embodiment can obtain the following effects.

[1]

The second image processing unit 54 generates the second image 530 or the like whose display manner is different from that of the first image 500. The display control unit 44 causes the monitor 400 to display the second image 530 or the like. This enables a physician to search for the region of interest 510 using the second image 530 or the like when noticing that the region of interest 510 has been overlooked by being notified that the region of interest 510 is detected.

[2]

Emphasis processing of the region of interest 510 is applied as the first image processing. In emphasis processing related to the second image processing, an emphasis degree is increased compared with an emphasis degree of the emphasis processing related to the first image processing. This may increase the visibility of the region of interest 510 in the second image 530 or the like.

[3]

The monitor 400 displays a plurality of second images including the second image 540 and the like with different acquisition timings. Thus, the region of interest 510 that has been overlooked in the endoscopic image 38 may be searched for from among the plurality of second images including the second image 540 and the like.

[4]

One or more second images, such as the second image 542, may be selected from among the plurality of second images including the second image 540 and the like with different acquisition timings. Thus, the second image 542 or the like to be used for searching for the region of interest 510 may be set from among the plurality of second images including the second image 540 and the like with different acquisition timings.

Image Processing Apparatus According to Third Embodiment

Figure 14:
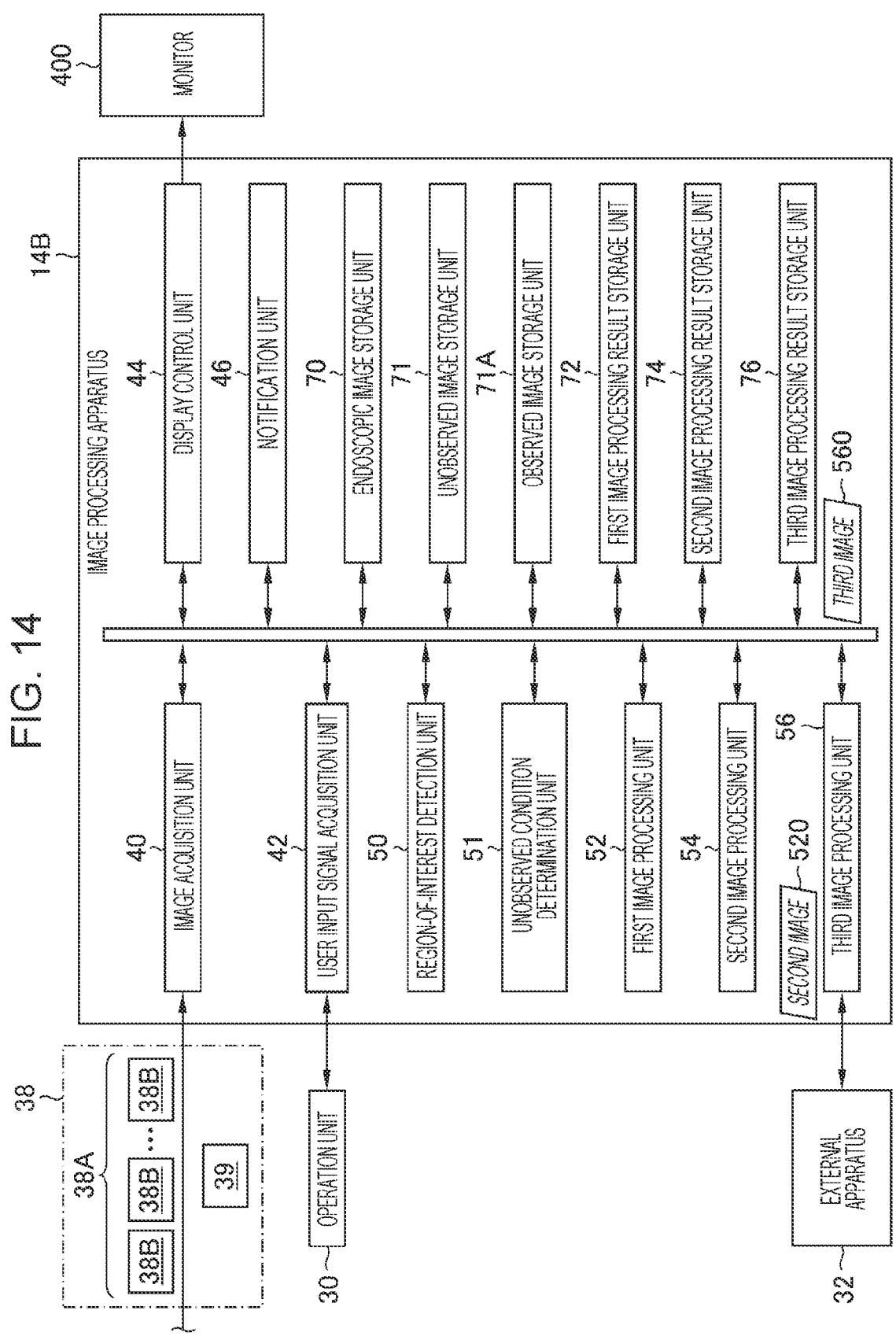
FIG. 14 is a functional block diagram of an image processing apparatus according to a third embodiment.

Next, an image processing apparatus according to the third embodiment will be described. FIG. 14 is a functional block diagram of the image processing apparatus according to the third embodiment. An image processing apparatus 14B illustrated in FIG. 14 is obtained by adding a third image processing unit 56 and a third image processing result storage unit 76 to the image processing apparatus 14A illustrated in FIG. 9.

The third image processing unit 56 performs third image processing on an unobserved image 39A, a second image 520, or the like to be displayed in the unobserved image display region 406. The second image 520 or the like herein indicates at least any of the second image 520 illustrated in FIG. 7, the second image 530 illustrated in FIG. 11, or the second image 540 and the second image 542 illustrated in FIG. 12. The same applies to the following description.

At least any of editing the unobserved image 39A, the second image 520, or the like, storing a third image generated by editing the unobserved image 39A, the second image 520, or the like, transmitting the unobserved image 39A, the second image 520, or the like to an external apparatus 32, deleting the unobserved image 39A, the second image 520, or the like, or rearranging a plurality of unobserved images 39A, a plurality of second images 520, or the like may be applied as the third image processing.

When the third image processing to be applied to the third image processing unit 56 is editing the unobserved image 39A, the second image 520, or the like, the third image processing result storage unit 76 stores a third image 560 generated by editing the unobserved image 39A, the second image 520, or the like. For example, enlarging and reducing the unobserved image 39A, the second image 520, or the like may be applied as editing of the unobserved image 39A, the second image 520, or the like.

Upon the user input signal acquisition unit 42 acquiring a user input signal indicating transmission of the unobserved image 39A, the second image 520, or the like to the external apparatus 32, the third image processing unit 56 transmits the unobserved image 39A, the second image 520, or the like to the external apparatus 32. A storage apparatus or the like communicably connected to the image processing apparatus 14B may be used as the external apparatus 32. Note that FIG. 14 illustrates transmission of the second image 520 and the like to the external apparatus 32.

Upon the user input signal acquisition unit 42 acquiring a user input signal indicating deletion of the unobserved image 39A, the second image 520, or the like, the third image processing unit 56 deletes the unobserved image 39A, the second image 520, or the like.

Upon the user input signal acquisition unit 42 acquiring a user input signal indicating rearranging of a plurality of unobserved images 39A, a plurality of second images 520, or the like, the third image processing unit 56 rearranges the unobserved image 39A, the second image 520, or the like.

Procedure of Image Processing Method According to Third Embodiment

Figure 15:
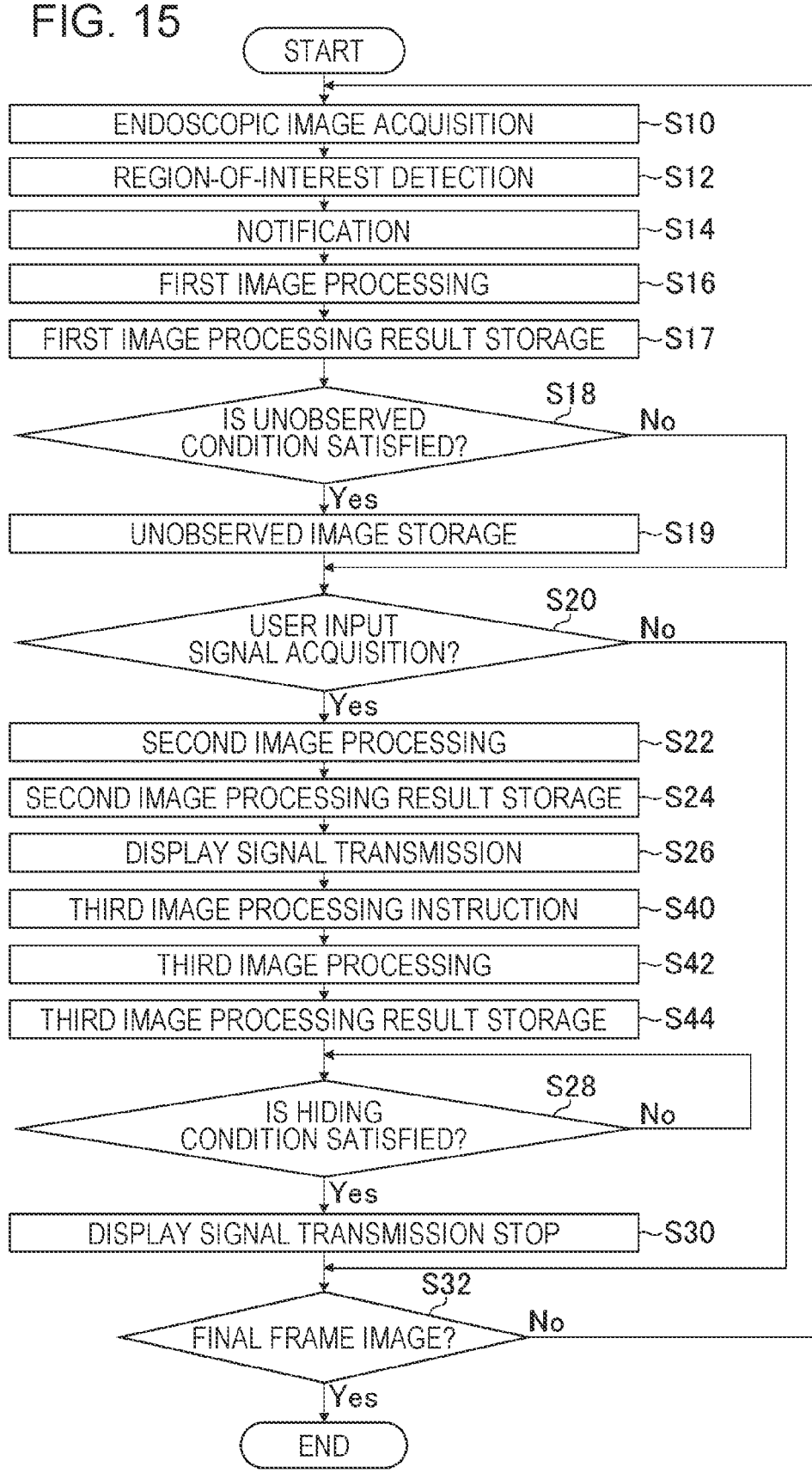
FIG. 15 is a flowchart illustrating a procedure of an image processing method according to the third embodiment.

FIG. 15 is a flowchart illustrating a procedure of an image processing method according to the third embodiment. FIG. 15 illustrates a procedure in a configuration in which editing the second image 530 is applied as third image processing. The flowchart illustrated in FIG. 15 is obtained by adding a third image processing instruction step S40, a third image processing step S42, and a third image processing result storage step S44 to the flowchart illustrated in FIG. 10.

The steps from the endoscopic image acquisition step S10 to the display signal transmission step S26 illustrated in FIG. 15 are the same as the steps from the endoscopic image acquisition step S10 to the display signal transmission step S26 illustrated in FIG. 10. After the display signal transmission step S26, the process advances to the third image processing instruction step S40.

In the third image processing instruction step S40, the user input signal acquisition unit 42 illustrated in FIG. 14 acquires an instruction signal for third image processing indicating processing details of the third image processing. Examples of acquisition of the instruction signal for third image processing include acquisition of a user input signal transmitted from the operation unit 30 illustrated in FIG. 14. After the third image processing instruction step S40, the process advances to the third image processing step S42.

In the third image processing step S42, the third image processing unit 56 performs the third image processing on the unobserved image 39A, the second image 520, or the like on the basis of the instruction signal. After the third image processing step S42, the process advances to the third image processing result storage step S44.

In the third image processing result storage step S44, the third image processing result storage unit 76 illustrated in FIG. 14 stores a processing result of the third image processing. After the third image processing result storage step S44, the process advances to the hiding condition determination step S28. If the third image processing is, for example, transmission of the unobserved image 39A, the second image 520, or the like to the external apparatus 32, or deletion of the unobserved image 39A, the second image 520, or the like, the third image processing result storage step S44 is skipped.

The steps from the hiding condition determination step S28 to the final frame image determination step S32 illustrated in FIG. 15 are the same as the steps from the hiding condition determination step S28 to the final frame image determination step S32 illustrated in FIG. 10.

Specific Example of Third Image Processing

Figure 16:
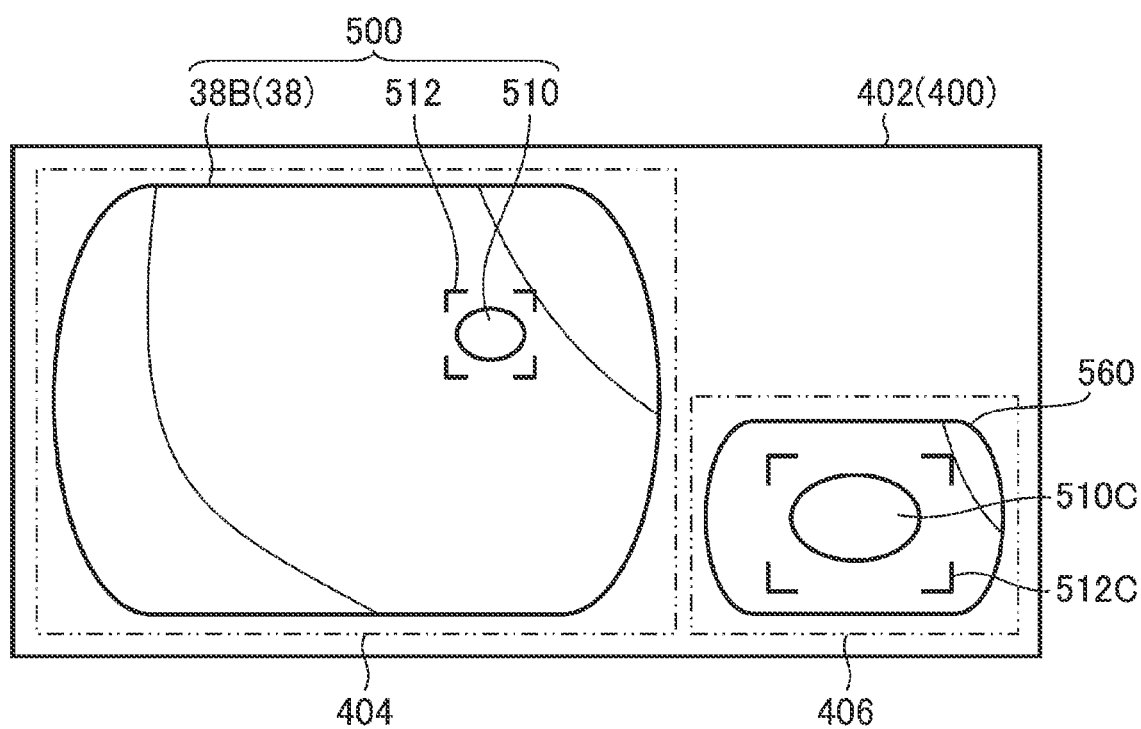
FIG. 16 is an explanatory diagram of an example of third image processing.

FIG. 16 is an explanatory diagram of an example of the third image processing. On the screen 402 illustrated in FIG. 16, the third image 560 is displayed instead of the second image 520 or the like illustrated in FIG. 7. On the screen 402, both the third image 560 and the second image 520 or the like may be displayed.

In the third image 560, the region of interest 510 in the second image 520 illustrated in FIG. 7 is enlarged. That is, the third image 560 illustrated in FIG. 16 includes a region of interest 510C obtained by enlarging the region of interest 510 illustrated in FIG. 7 and a bounding box 512C obtained by enlarging the bounding box 512 illustrated in FIG. 7.

Effects of Third Embodiment

The image processing apparatus 14B and the image processing method according to the third embodiment can obtain the following effects.

[1]

The image processing apparatus 14B includes the third image processing unit 56 that performs third image processing on the unobserved image 39A, the second image 520, or the like. Thus, the unobserved image 39A, the second image 520, or the like may be edited, for example.

[2]

Editing the unobserved image 39A, the second image 520, or the like, storing a result of editing of the unobserved image 39A, the second image 520, or the like, transmitting the unobserved image 39A, the second image 520, or the like to an external apparatus, deleting the unobserved image 39A, the second image 520, or the like, and rearranging a plurality of unobserved images 39A, a plurality of second images 540, or the like in an embodiment of displaying the unobserved images 39A, a plurality of second images 540, or the like may be applied as the third image processing. Thus, the unobserved image 39A, the second image 520, or the like may be edited.

MODIFICATION EXAMPLES OF ENDOSCOPE SYSTEM

Modification Examples of Illumination Light

Examples of a medical image acquirable by using the endoscope system 10 illustrated in the embodiments include a normal-light image obtained by radiating light in a white range or light in a plurality of wavelength ranges as the light in the white range.

Other examples of a medical image acquirable by using the endoscope system 10 illustrated in the embodiments include an image obtained by radiating light in a specific wavelength range. A range narrower than the white range is applicable as the specific wavelength range. The following modification examples are applicable.

First Modification Example

A first example of the specific wavelength range is a blue range or a green range in a visible range. The wavelength range of the first example includes a wavelength range of 390 nm or more and 450 nm or less or a wavelength range of 530 nm or more and 550 nm or less, and the light of the first example has a peak wavelength in the wavelength range of 390 nm or more and 450 nm or less or the wavelength range of 530 nm or more and 550 nm or less.

Second Modification Example

A second example of the specific wavelength range is a red range in the visible range. The wavelength range of the second example includes a wavelength range of 585 nm or more and 615 nm or less or a wavelength range of 610 nm or more and 730 nm or less, and the light of the second example has a peak wavelength in the wavelength range of 585 nm or more and 615 nm or less or the wavelength range of 610 nm or more and 730 nm or less.

Third Modification Example

A third example of the specific wavelength range includes a wavelength range in which an absorption coefficient is different between oxyhemoglobin and deoxyhemoglobin, and the light of the third example has a peak wavelength in the wavelength range in which the absorption coefficient is different between oxyhemoglobin and deoxyhemoglobin. The wavelength range of this third example includes a wavelength range of 400±10 nm, a wavelength range of 440±10 nm, a wavelength range of 470±10 nm, or a wavelength range of 600 nm or more and 750 nm or less, and the light of the third example has a peak wavelength in the wavelength range of 400±10 nm, the wavelength range of 440±10 nm, the wavelength range of 470±10 nm, or the wavelength range of 600 nm or more and 750 nm or less.

Fourth Modification Example

A fourth example of the specific wavelength range is a wavelength range of excitation light that is used to observe fluorescence emitted by a fluorescent substance in a living body and excites this fluorescent substance. For example, the specific wavelength range of the fourth example is a wavelength range of 390 nm or more and 470 nm or less. Note that observation of fluorescence may be referred to as fluorescence observation.

Fifth Modification Example

A fifth example of the specific wavelength range is a wavelength range of infrared light. The wavelength range of this fifth example includes a wavelength range of 790 nm or more and 820 nm or less or a wavelength range of 905 nm or more and 970 nm or less, and the light of the fifth example has a peak wavelength in the wavelength range of 790 nm or more and 820 nm or less or the wavelength range of 905 nm or more and 970 nm or less.

Generation Examples of Special-Light Image

The processor apparatus 200 may generate a special-light image having information in the specific wavelength range on the basis of a normal-light image obtained through imaging using white light. Note that the term "generation" used herein includes "acquisition". In this case, the processor apparatus 200 functions as a special-light image acquisition unit. The processor apparatus 200 obtains a signal of the specific wavelength range by performing calculation based on color information of red, green, and blue or color information of cyan, magenta, and yellow included in the normal-light image.

In addition, cyan, magenta, and yellow are sometimes referred to as CMY by using the respective initials.

Examples of Generating Feature-Quantity Image

As the medical image, a feature-quantity image may be generated by using a calculation based on at least any of a normal-light image or a special-light image. The normal-light image is obtained by radiating light in the white range or light in a plurality of wavelength ranges as the light in the white range. The special-light image is obtained by radiating light in the specific wavelength range.

Application Examples to Program Causing Computer to Function as Image Processing Apparatus The above-described image processing apparatus and image processing method can be configured as a program that causes a computer to implement functions corresponding to the units of the image processing apparatus or the steps of the medical image processing method.

For example, it is possible to configure a program that causes a computer to implement an image acquisition function, a display signal transmission function, a region-of-interest detection function, an unobserved image storage function, and a user input signal acquisition function.

The image acquisition function corresponds to the image acquisition unit 40 and the endoscopic image acquisition step S10. The display signal transmission function corresponds to the display control unit 44 and the display signal transmission step S26. The region-of-interest detection function corresponds to the region-of-interest detection unit 50 and the region-of-interest detection step S12.

The unobserved image storage function corresponds to the unobserved image storage unit 71 and the unobserved condition determination step S18. The user input signal acquisition function corresponds to the user input signal acquisition unit 42 and the user input signal acquisition determination step S20.

The program may include first image processing function corresponding to the first image processing unit 52 and the first image processing step S16. The program may include a first image processing result storage function corresponding to the first image processing result storage unit 72 and the first image processing result storage step S17.

The program may include a second image processing function corresponding to the second image processing unit 54 and the second image processing step S22. The program may include a second image processing result storage function corresponding to the second image processing result storage unit 74 and the second image processing result storage step S24. The program may include a third image processing function corresponding to the third image processing unit 56 and the third image processing step S42.

A program that causes a computer to implement the above-described image processing functions may be stored on a computer-readable information storage medium which is a non-transitory tangible information storage medium, and the program may be provided using the information storage medium.

In addition, instead of the configuration in which the program is stored on a non-transitory information storage medium and is provided, a configuration in which a program signal is provided via a communication network may be employed.

Regarding Combination of Embodiments, Modifications, Etc.

The constituent elements described in the embodiments above and the constituent elements described in the modifications can be appropriately used in combination, and some of the constituent elements can be replaced.

In the embodiments of the present invention described above, the constituent elements can be appropriately changed, added, or deleted without departing from the gist of the present invention. The present invention is not limited to the embodiments described above, and various modifications can be made by a person having the ordinary skill in the art within the technical sprit of the present invention.

REFERENCE SIGNS LIST 10 endoscope system
14 image processing apparatus
14A image processing apparatus
14B image processing apparatus
38 endoscopic image
38A moving image
38B frame image
39 still image
39A unobserved image
40 image acquisition unit
42 user input signal acquisition unit
44 display control unit
46 notification unit
50 region-of-interest detection unit
51 unobserved condition determination unit
52 first image processing unit
54 second image processing unit
56 third image processing unit
70 endoscopic image storage unit
71 unobserved image storage unit
71A observed image storage unit
72 first image processing result storage unit
74 second image processing result storage unit
76 third image processing result storage unit
100 endoscope main body
102 handheld operation part
104 insertion part
106 universal cable
108 light guide connector
112 soft part
114 bending part
116 tip rigid part
116A tip-side end surface
123 illumination part
123A illumination lens
123B illumination lens
126 forceps port
130 imaging part
132 imaging lens
134 imaging element
136 driving circuit
138 analog front end
141 air/water supply button
142 suction button
143 function button
144 imaging button
170 light guide
200 processor apparatus
202 image input controller
204 image processing unit
205 communication control unit
206 video output unit
207 storage unit
208 operation unit
209 voice processing unit
209A speaker
210 CPU
211 ROM
212 RAM
300 light source apparatus
310 light source
310B blue light source
310G green light source
310R red light source
330 aperture diaphragm
340 condensing lens
350 light source control unit
400 monitor
402 screen
404 observation image display region
406 unobserved image display region
500 first image
510 region of interest
510A region of interest
510B region of interest
510C region of interest
512 bounding box
512A bounding box
512B bounding box
512C bounding box
520 second image
530 second image
532 bounding box
540 second image
542 second image
560 third image
S10 to S44 steps of image processing method

What is claimed is:

1. A medical image processing apparatus comprising one or more processors configured to:
acquire an observation image of a subject;
detect a region of interest from frame images constituting the observation image;
determine whether each of the frame images in which the region of interest has been detected satisfies an unobserved condition indicating that the region of interest having been overlooked by a user is contained;
store, in a storage, an unobserved frame image that is one of the frame images satisfying the unobserved condition;
transmit, to a display apparatus, a first display signal indicating the observation image and a second display signal indicating the unobserved frame image; and
determine sameness of the region of interest in the unobserved frame image and the region of interest in the observation image on the basis of a result of comparison between a feature quantity of the region of interest in the unobserved frame image and a feature quantity of the region of interest in the observation image, and stop transmitting the second display signal when determining that the region of interest in the unobserved frame image and the region of interest in the observation image are the same.

2. The medical image processing apparatus according to claim 1, wherein the one or more processors are configured to, in a case where a number of frame images including the same region of interest within a predetermined period is less than or equal to a predetermined number, determine that the unobserved condition is satisfied.

3. The medical image processing apparatus according to claim 1, wherein the one or more processors are configured to, in a case where a change amount between frame images is greater than or equal to a predetermined threshold value, determine that the unobserved condition is satisfied.

4. The medical image processing apparatus according to claim 1, wherein the one or more processors are configured to, in a case where the same region of interest remains in a given region on a screen within a predetermined period, determine that the unobserved condition is satisfied.

5. The medical image processing apparatus according to claim 1, wherein the one or more processors are configured to:
    acquire a user input signal transmitted in response to a user operation; and
    upon acquiring a user input signal indicating displaying of an unobserved region of interest, transmit the second display signal indicating the unobserved image to the display apparatus.

6. The medical image processing apparatus according to claim 5, wherein the one or more processors are configured to:
    perform first image processing on the detected region of interest to generate a first image; and
    transmit, to the display apparatus, a display signal indicating the first image as the first display signal.

7. The medical image processing apparatus according to claim 6, wherein the one or more processors are configured to:
    perform second image processing on the unobserved image to generate a second image; and
    transmit, to the display apparatus, a display signal indicating the second image as the second display signal.

8. The medical image processing apparatus according to claim 7, wherein the one or more processors are configured to:
    perform emphasis processing of the region of interest on the observation image; and
    perform emphasis processing on the unobserved image to increase an emphasis degree compared with an emphasis degree of the emphasis processing of the region of interest on the observation image.

9. The medical image processing apparatus according to claim 7, wherein the one or more processors are configured to:
    perform the second image processing on each of a plurality of unobserved images; and
    transmit, to the display apparatus, a display signal corresponding to each of a plurality of second images as the second display signal.

10. The medical image processing apparatus according to claim 9, wherein the one or more processors are configured to select one or more unobserved images from among the plurality of unobserved images to be displayed on the display apparatus or select one or more second images from among the plurality of second images to be displayed on the display apparatus.

11. The medical image processing apparatus according to claim 7, wherein the one or more processors are configured to perform third image processing on the unobserved image or a processing result of the second image processing to be displayed on the display apparatus.

12. The medical image processing apparatus according to claim 11, wherein the one or more processors are configured to store a processing result of the third image processing in the storage.

13. The medical image processing apparatus according to claim 11, wherein the one or more processors are configured to edit the unobserved image upon acquiring a user input signal indicating editing of the unobserved image or edit the second image upon acquiring a user input signal indicating editing of the second image.

14. The medical image processing apparatus according to claim 11, wherein the one or more processors are configured to transmit the unobserved image to an external apparatus upon acquiring a user input signal indicating transmission of the unobserved image to the external apparatus or transmit the second image to an external apparatus upon acquiring a user input signal indicating transmission of the second image to the external apparatus.

15. The medical image processing apparatus according to claim 11, wherein the one or more processors are configured to rearrange a plurality of unobserved images upon acquiring a user input signal indicating rearranging of the plurality of unobserved images or rearrange a plurality of second images upon acquiring a user input signal indicating rearranging of the plurality of second images.

16. The medical image processing apparatus according to claim 11, wherein the one or more processors are configured to delete the unobserved image upon acquiring a user input signal indicating deletion of the unobserved image or delete the second image upon acquiring a user input signal indicating deletion of the second image.

17. The medical image processing apparatus according to claim 5, wherein the one or more processors are configured to stop transmitting the second display signal when the unobserved region of interest is displayed on the display apparatus.

18. The medical image processing apparatus according to claim 1, wherein the one or more processors are configured to stop transmitting the second display signal after an elapse of a predetermined period from a transmission timing of the second display signal.

19. The medical image processing apparatus according to claim 1, further comprising a user operation receiver operated by a user,
    wherein the one or more processors are configured to acquire a user input signal transmitted in response to an operation performed by the user on the user operation receiver.

20. The medical image processing apparatus according to claim 1, further comprising a voice receiver that receives a voice of a user,
    wherein the one or more processors are configured to acquire a user input signal indicating the voice of the user received by the voice receiver.

21. The medical image processing apparatus according to claim 1, wherein the one or more processors are configured to store, in the storage, an observed image indicating that the region of interest has been observed from the frame image in which the region of interest is detected.

22. The medical image processing apparatus according to claim 1, further comprising a notifier,
    wherein the one or more processors are configured to notify, through the notifier, detection of the region of interest in the observation image.

23. An endoscope system comprising:
    an endoscope;
    an endoscope control apparatus configured to control the endoscope; and
    a medical image processing apparatus configured to perform processing on an endoscopic image acquired by the endoscope,
    wherein the medical image processing apparatus comprises one or more processors configured to:
    acquire an observation image of a subject;
    detect a region of interest from frame images constituting the observation image;
    determine whether each of the frame images in which the region of interest has been detected satisfies an unobserved condition indicating that the region of interest having been overlooked by a user is contained;

store, in a storage, an unobserved frame image that is one of the frame images satisfying the unobserved condition;

transmit, to a display apparatus, a first display signal indicating the observation image and a second display signal indicating the unobserved frame image; and determine sameness of the region of interest in the unobserved frame image and the region of interest in the observation image on the basis of a result of comparison between a feature quantity of the region of interest in the unobserved frame image and a feature quantity of the region of interest in the observation image, and stop transmitting the second display signal when determining that the region of interest in the unobserved frame image and the region of interest in the observation image are the same.

24. A medical image processing method comprising:

acquiring an observation image of a subject;

detecting a region of interest from frame images constituting the observation image;

determining whether each of the frame images in which the region of interest has been detected satisfies an unobserved condition indicating that the region of interest having been overlooked by a user is contained;

storing an unobserved frame image that is one of the frame images satisfying the unobserved condition;

transmitting, to a display apparatus, a first display signal indicating the observation image and a second display signal indicating the unobserved frame image; and determining sameness of the region of interest in the unobserved frame image and the region of interest in the observation image on the basis of a result of comparison between a feature quantity of the region of interest in the unobserved frame image and a feature quantity of the region of interest in the observation image, and stopping transmitting the second display signal when determining that the region of interest in the unobserved frame image and the region of interest in the observation image are the same.

25. A non-transitory computer-readable recording medium which stores thereon a command for causing a computer to execute the medical image processing method according to claim 24 upon the computer reading the command stored in the recording medium.

* * * * *